United States Patent
Hjorleifsdottir et al.

(10) Patent No.: US 7,303,901 B2
(45) Date of Patent: Dec. 4, 2007

(54) THERMOSTABLE RNA LIGASE FROM THERMUS PHAGE

(75) Inventors: Sigridur Hjorleifsdottir, Reykjavik (IS); Audur Thorisdottir, Lund (NO); Arnthor Aevarsson, Hveragerdi (IS); Gudmundur Oli Hreggvidsson, Reykjavik (IS); Thorarinn Blondal, Gardabaer (IS)

(73) Assignee: Prokaria Ehf., Reykjavik (IS)

( * ) Notice: Subject to any disclaimer, the term of this patent is extended or adjusted under 35 U.S.C. 154(b) by 0 days.

(21) Appl. No.: 11/084,220

(22) Filed: Mar. 18, 2005

(65) Prior Publication Data

US 2005/0266439 A1    Dec. 1, 2005

Related U.S. Application Data

(63) Continuation of application No. PCT/IS03/00030, filed on Sep. 19, 2003.

(60) Provisional application No. 60/412,461, filed on Sep. 20, 2002.

(51) Int. Cl.
*C12N 9/00* (2006.01)
*C12N 1/20* (2006.01)
*C12N 15/00* (2006.01)
*C12P 19/34* (2006.01)
*C07H 21/04* (2006.01)

(52) U.S. Cl. .............. 435/183; 435/91.52; 435/252.32; 435/320.1; 536/23.2

(58) Field of Classification Search ............. 435/91.52, 435/183, 252.32, 320.1; 536/23.2
See application file for complete search history.

(56) References Cited

FOREIGN PATENT DOCUMENTS

WO    WO 00/75335    * 12/2000

OTHER PUBLICATIONS

Rand et al. Accession A01202; S08604. Feb. 28, 1986.*
Blondal et al. Nucleic Acids Res. Dec. 15, 2003;31(24):7247-54.*

* cited by examiner

*Primary Examiner*—Ponnathapu Achutamurthy
*Assistant Examiner*—Christian L. Fronda
(74) *Attorney, Agent, or Firm*—Schwegman, Lundberg & Woessner P.A.

(57) ABSTRACT

An RNA ligase derived from bacteriophage TS2126 which infects *Thermus scotoductus*, nucleic acids comprising nucleotide sequences of open reading frame (ORF) and polypeptides encoded by the nucleic acids, are described.

4 Claims, 15 Drawing Sheets

ORF of RNA-ligase from TS2126 (e.g. SEQ ID NO 1)

ATGAGCTCTTTGGCCCCGTGGAGGACTACCTCCTGGAGCCCGCTTGGGAGCCCGCCTAGCCTCGAGGACGCCCTCCG
CCTCGCCCGGACCACCAGGGCCTTCGCGGTGCGGCGGGACGGGGAGGGGCGGGCCCTCGTGACCTACCTCTACGGCA
CCCCGGAGCTCTTCAGCCTCCCGGGGGCAAGGGAGCTCCGGGGCATCGTCTACCGGGAGGAGGACGGCACCGTGCTC
AGCCGCCCCTTCCACAAGTTCTTCAACTTCGGGGAGCCCCTGGCCCCGGGGGAGGAGGCCTTCAAGGCCTTCCGGGA
CAGCATGGTCCCCCTCTTCGTGGCCGAGAAGGTGGACGGCTATCTGGCCCAGGCCTACCTGGACGGGGGCGAGCTCC
GCTTCGCCTCCCGGCACTCCCTGAACCCGCCCCTGGTAGGGCGCTCCTGCGCAAGGCCGTGGACGAGGAGGCGATG
GCTCGCCTGGGGAAGCTCCTCGCCGCCGAAGGGGGAAGGTGGACGGCGCTTTTGGAGGTGGTGGACCCCGAGGCCCC
GGTGATGGTGCCCTACCAGGAGCCCGGGGTCTACCTCCTGGCCCTGAGGAGCATCGGGGAGGGGCACTACCTCCTCC
CCGGGGTCCACTTCCCCCTGCCCGAGGCGCTCCGCTACGTGCGGTGGGAGCCCAGGATGGATTTTGACCCCCACCGC
TTCCGGGGGGAGATCAGGGACCTCCAGGGGGTGGAGGGGTACGTGGTCACGGACGGGGCAGAGTTCGTCAAGTTCAA
GACAGGGTGGGCCTTCCGCCTCGCCCGCTTCCTCATGGACCCGGAGGGGGTGTTCCTCGAGGCCTACGCCGAGGACC
GCCTAGACGACCTCGTGGGCGCCCTCGCGGGGCGGGAGGACCTCCTGCGGGCGGTGGCCAGGGCCCAGGACTACCTC
GCCGGGCTCTACGGGGAAGCGGTGGGCGCGGGGACGCCCTGAGGCGGATGGGCCTCCCCCGGAAGGAGGCCTGGGC
CCGGGTGCAGGAGGAGGCCGGGCGCTGGGGCGGCTTCGCCCCCGCCTACGCCCGGCGGCCATGGCGGCCTACGAGG
GGGGAGAGGCGCGCGAGGCCTTCCTGGTGGAGCTCAGGAAGAGGAGCGCGCGGAAGGCCCTCGAGGCGCTCCACCTC
TTCCCCCGGGTGGGCGGGGAGCTTAGGGGGTGA

FIG. 1

Sequence alignment of T4 RNA-ligase and ORF-1.

>ref|NP_049839.1| (NC_000866) RNA ligase [Enterobacteria phage T4]
sp|P00971|RLIG_BPT4 RNA ligase
pir||LQBPR4 RNA ligase (ATP) (EC 6.5.1.3) - phage T4
emb|CAA25107.1| (X00365) RNA ligase [Enterobacteria phage T4]
gb|AAD42514.1|AF158101_101 (AF158101) RNA ligase [Enterobacteria phage T4]
          Length = 374

Score = 74.5 bits (180), Expect = 3e-12
Identities = 78/273 (28%), Positives = 118/273 (42%), Gaps = 11/273 (4%)
Frame = +1

```
Query: 118 GEGRALVTYLYGTPELFSLPGARELRGIVYR---EEDGTVLSRPFHKFFNFGEPLAPGEE 288
           G   + +Y Y +   + LP A E RGI++    E+   + SRP  KFFN  E
Sbjct: 29  GRTYRIFSYNYASYSDWLLPDALECRGIMFEMDGEKPVRIASRPMEKFFNLNE------N 82

Query: 289 AFKAFRDSMVPLFVAEKVDGYLAQAYLDGGELRFASRHSLNPP---LVGALLRKAVDEEA 459
            F  D    ++  K DG L    YLDG E+ F S+ S+        +   +L
Sbjct: 83  PFTMNIDLNDVDYILTKEDGSLVSTYLDGDEILFKSKGSIKSEQALMANGILMNINHHRL 142

Query: 460 MARLGKLLAAEGGRWTALLEVVDPEAPVMVPYQEPGVYLLALRSIGEGHYLLPGVHFPLP 639
           + RL +L   AE G +TA   E V P   +++ YQE  + LL +R   G Y+     +
Sbjct: 143 RDRLKEL--AEDG-FTANFEFVAPTNRIVLAYQEMKIILLNVRENETGEYISYDDIYKDA 199

Query: 640 EALRYVRWEPRMDFDPHRFRGEIRDLQGVEGY--VVTDGAEFVKFKTGWAFRL---ARFL 804
            Y+    R + D  ++   E ++  + +EGY  V+ DG+ F K K+ W   L        L
Sbjct: 200 TLRPYL--VERYEIDSPKWIEEAKNAENIEGYVAVMKDGSHF-KIKSDWYVSLHSTKSSL 256

Query: 805 MDPEGVFLEAYAEDRLDDLVGALAGREDLLRAV 903
           +PE +F +    + DDL   A E  R +
Sbjct: 257 DNPEKLF-KTIIDGASDDLKAMYADDEYSYRKI 288
```

FIG. 2

Bacteriophage TS2126 RNA ligase, amino acid sequence (e.g. SEQ ID NO 2):
>RNA ligase from Thermus phage TS2126
MSSLAPWRTTSWSPLGSPPSLEDALRLARTTRAFAVRRDGEGRALVTYLYGTPELFSLPG
ARELRGIVYREEDGTVLSRPFHKFFNFGEPLAPGEEAFKAFRDSMVPLFVAEKVDGYLAQ
AYLDGGELRFASRHSLNPPLVGALLRKAVDEEAMARLGKLLAAEGGRWTALLEVVDPEAP
VMVPYQEPGVYLLALRSIGEGHYLLPGVHFPLPEALRYVRWEPRMDFDPHRFRGEIRDLQ
GVEGYVVTDGAEFVKFKTGWAFRLARFLMDPEGVFLEAYAEDRLDDLVGALAGREDLLRA
VARAQDYLAGLYGEAVGAGDALRRMGLPRKEAWARVQEEAGRWGGFAPAYARAAMAAYEG
GEAREAFLVELRKRSARKALEALHLFPRVGGELRG*

FIG. 3

Enterobacteria phage T4 RNA ligase, amino acid sequence (e.g. SEQ ID NO 3):
>gi|133093|sp|P00971|RLIG_BPT4 RNA ligase
MQELFNNLMELCKDSQRKFFYSDDVSASGRTYRIFSYNYASYSDWLLPDALECRGIMFEMDGEKPVRIAS
RPMEKFFNLNENPFTMNIDLNDVDYILTKEDGSLVSTYLDGDEILFKSKGSIKSEQALMANGILMNINHH
RLRDRLKELAEDGFTANFEFVAPTNRIVLAYQEMKIILLNVRENETGEYISYDDIYKDATLRPYLVERYE
IDSPKWIEEAKNAENIEGYVAVMKDGSHFKIKSDWYVSLHSTKSSLDNPEKLFKTIIDGASDDLKAMYAD
DEYSYRKIEAFETTYLKYLDRALFLVLDCHNKHCGKDRKTYAMEAQGVAKGAGMDHLFGIIMSLYQGYDS
QEKVMCEIEQNFLKNYKKFIPEGY

FIG. 4

The pH optimum of TS2126 RNA ligase in MOPS buffer was 7.5

The TS2126 RNA ligase shows over 90% activity from 55-70°C

Thermostability of the TS2126 RNA ligase

Effects of covalent cations on the RNA ligase reaction

Effect of ATP to the activity of TS2126 RNA ligase

Comparison of the activity of TS2126 and T4 RNA ligases

Effect of protein concentration on the activity of TS2126 RNA ligase

A: lane 3: TS RNA ligase, lane 4: T4 RNA ligase, lane 5: cDNA control, lane 6: PCR control
B: lanes 8-12: Beta actin cDNA controls 200 bp 5' inverse beta actin PCR product over the borders of the ligation The results from the inverse beta actin PCR show clearly that TS2126 RNA ligase can be used for cDNA ligation

THERMOSTABLE RNA LIGASE FROM THERMUS PHAGE

CROSS-REFERENCE TO RELATED APPLICATIONS

This application is a continuation under 35 U.S.C. 111(a) of PCT/IS2003/000030, filed Sep. 19, 2003 and published in English on Apr. 1, 2004 as WO 2004/027054 A1, which claimed priority under 35 U.S.C. 119(e) of U.S. Provisional Application Ser. No.: 60/412,461, filed Sep. 20, 2002, which applications and publication are incorporated herein by reference.

BACKGROUND OF THE INVENTION

RNA ligase is abundant in T4-infected cells and has been purified in high yields. Bacteriophage T4 RNA ligase catalyzes the ATP-dependent ligation of a 5'-phosphoryl-terminated nucleic acid donor (i.e., RNA or DNA) to a 3'-hydroxyl-terminated nucleic acid acceptor. The reaction can be either intramolecular or intermolecular, i.e., the enzyme catalyzes the formation of circular DNA/RNA, linear DNA/RNA dimers, and RNA-DNA or DNA-RNA block copolymers. The use of a 5'-phosphate, 3'-hydroxyl terminated acceptor and a 5'-phosphate, 3'-phosphate terminated donor limits the reaction to a unique product. Thus, RNA ligase can be an important tool in the synthesis of DNA of defined sequence (McCoy & Gumport, *Biochemistry* 19:635-642 (1980); Sugino, A. et al., *J. Biol. Chem.* 252:1732-1738 (1977)).

The practical use of T4 RNA ligase has been demonstrated in many ways. Various ligation-anchored PCR amplification methods have been developed, where an anchor of defined sequence is directly ligated to single strand DNA (following primer extension, e.g., first strand cDNA). The PCR resultant product is amplified using primers specific for both the DNA of interest and the anchor (Apte, A. N., and P. D. Siebert, *BioTechniques*, 15:890-893 (1993); Troutt, A. B., et al., *Proc. Natl. Acad. Sci. USA*, 89:9823-9825 (1992); Zhang, X. H., and V. L. Chiang, *Nucleic Acids Res.*, 24:990-991(1996)). Furthermore, T4 RNA ligase has been used in fluorescence-, isotope- or biotin-labeling of the 5'-end of single stranded DNA/RNA molecules (Kinoshita Y., et al., *NucleiAcid Res.*, 25: 3747-3748 (1997)), synthesis of circular hammer head ribozymes (Wang, L., and D. E. Ruffner. *Nucleic Acids Res.*, 26:2502-2504 (1998)), synthesis of dinucleoside polyphosphates (Atencia, E. A., et al., *Eur. J. Biochem.*, 261: 802-811 (1999)), and for the production of composite primers (Kaluz, S., et al., *BioTechniques*, 19:182-186 (1995)).

RNA ligase activity was originally identified as activity induced through infection of *E. coli* by T-even bacteriophages (Silber, R et al., *Proc. Natl. Acad. USA*, 69: 3009-3013 (1972)). The RNA ligase from bacteriophage T4 is the product of gene 63 (Snopek, T. J., et al., *Proc. Natl. Acad. Sci. USA*, 74:3355-3359 (1977)) and is the best characterized RNA ligase of very few known homologous RNA ligases.

The properties of RNA ligase from bacteriophage T4 have been extensively studied including its ability to catalyze reactions with various substrates (for review see Gumport and Uhlenbeck, in "Gene Amplification and Analysis," *Vol. II: Analysis of Nucleic Acid Structure by Enzymatic Methods*, Chirikjian and Papas, eds. Elsevier North Holland, Inc. (1980)). In general, the T4 RNA ligase catalyzes the ATP-dependent formation of a phosphodiester bond between a 3'-hydroxyl nucleic acid acceptor and a 5'-phosphate nucleic acid donor. This includes ligation of two oligonucleotides as well as the circularization of a single oligonucleotide. T4 RNA ligase can use single-stranded nucleic acids as substrates and does not require a complementary template strand to align donor phosphates with acceptor hydroxyls.

5'-phosphorylated oligonucleotides are appropriate donors for the ATP-dependent T4 RNA ligase reaction but the minimal donor is a nucleoside 3',5'-biphosphate (pNp). The suitable minimal acceptor molecules for the T4 RNA ligase reaction are trinudeoside diphosphates.

T4 RNA ligase is adenylated in the presence of ATP thereby forming a covalent bond between AMP and a lysyl residue. The adenylyl group may then be transferred from the enzyme to the 5'-phosphate of an acceptor nucleic acid. T4 RNA ligase can accept ATP analogues and adenylate nucleic acid substrates with the nucleotide analogue. T4 RNA ligase is able to catalyze a class of reactions that do not require ATP. The enzyme is able to accept a wide variety of ADP derivatives as substrates and join the extra moiety of the ADP derivative to a nucleic acid acceptor with the elimination of AMP. Examples of ADP derivative of this type include ADP-riboflavin and ADP-hexylamine-blotin (see further Gumport and Uhlenbeck, ibid.)

T4 RNA ligase has a greater affinity for RNA than DNA. Although RNA and DNA are equally reactive as donors, DNA is a much less efficient acceptor than RNA. The efficiency of the RNA ligase reaction is also affected by the nucleotide composition of the acceptor with oligo(A) the most efficient acceptor. RNA molecules are also good acceptors for the T4 RNA ligase.

The 5'-phosphate of yeast tRNA$^{Phe}$ is a very poor donor for T4 RNA ligase, indicating that secondary or tertiary structure in the RNA donor molecule is inhibiting the ligase reaction. In contrast, DNA restriction fragments are good donors and little difference is observed between DNA restriction fragments with 5'-staggered ends and blunt ends. On the other hand, the presence of a secondary structure of an RNA acceptor molecule has little effect on the reaction. The 5'-cap (m$^7$ G$^{5'}$ppp-5'), which is normally formed through addition of methylated guanosine to the 5' end of eukaryotic mRNA, is neither an acceptor nor a donor for the T4 RNA ligase reaction (Gumport and Uhlenbeck, ibid.).

T4 RNA ligase is a versatile enzyme with new properties continuing to be discovered. For example, T4 RNA ligase has recently been shown to be able catalyze reaction between a 3'-phosphate donor and 5'-hydroxyl acceptor in addition to previously characterized reaction of 5'-phosphate donor and 3'-hydroxyl acceptor (U.S. Pat. No. 6,329,177). T4 RNA ligase has also been shown to have template-mediated DNA ligase activity. Reportedly, the T4 RNA ligase can ligate ends of DNA strands hybridized to RNA, even more efficiently than T4 DNA ligase (U.S. Pat. No. 6,368,801).

Enzymes having RNA ligase activity, but which are apparently not related to the T4 RNA ligase and other homologous proteins in the small family of viral RNA ligases, have been identified. These enzymes may have relatively strict substrate specificity whereas the activity of T4 RNA ligase is the most general RNA joining activity known.

The RNA ligases of T-even bacteriophages apparently belong to a very small family of homologous enzymes. However, it is likely that this is a subfamily of much larger superfamily of ligases including DNA ligases and mRNA capping enzymes (Shuman, S. and Schwer, B., *Mol. Microbiol.*, 17:405-410 (1995); Timson, D. J., et al., *Mut. Res.*, 460:301-318 (2000)). Until recently, the only clearly identifiable relatives of T4 RNA ligase, found through sequence comparisons (ex. with BLAST software), were from bacteriophage RB69 and *Autographa californica nuclearpolyhedrosis* virus. As disclosed in a previous patent applications (U.S. patent application Ser. No. 09/585,858; PCT Application No. PCT/1800/00893; European Application No. 00938977.6), the discovery of a bacteriophage from the thermophilic bacterial host *Rhodothernus marinus* and the subsequent genome sequencing identified a potential new RNA ligase belonging to this family according to the amino acid sequence of the predicted gene product of a particular open reading frame.

The use of thermostable enzymes has revolutionized the field of recombinant DNA technology. Thermostable enzymes, foremost DNA polymerases used in amplification of DNA, are of great importance in the research industry today. In addition, thermophilic enzymes are also used in commercial settings (e.g., proteases and lipases used in washing powder, hydrolytic enzymes used in bleaching). Identification of new thermophilic enzymes will facilitate continued DNA research as well as assist in improving commercial enzyme-based products.

SUMMARY OF THE INVENTION

This invention pertains to an RNA ligase enzyme from a bacteriophage that infects *Thermus scotoductus* (a thermophilic organism), bacteriophage TS2126, which can be isolated from its native environment or can be recombinantly produced. The invention pertains to nucleic adds of TS2126 RNA ligase as is shown in FIG. 1. The invention further pertains to isolated polypeptides encoded by these nucleic acids (e.g., SEQ ID NO: 2), polypeptides which have at least 30% sequence identity with the amino acid sequence of SEQ ID NO: 2 and active derivatives or fragments of these polypeptides. The invention also pertains to DNA constructs containing the isolated nucleic acid molecules operatively linked to a regulatory sequence; and also to host cells comprising the DNA constructs.

The TS2126 bacteriophage RNA ligase has been found to be significantly more thermostable than those of other (e.g., mesophilic) bacteriophages, such as the T4 RNA ligase of *Escherichia coli*. The enhanced stability of the enzymes and proteins of TS2126 bacteriophage allows their use under temperature conditions which would be prohibitive for other enzymes, thereby increasing the range of conditions which can be employed and also the type of methods. For example, amplification of mRNA and synthesis of cDNA often involve the use of a complex mixture of RNA containing RNA molecules with various stable secondary structures, which inhibits the action of T4 RNA ligase. The negative influence of secondary structure has been shown using well-defined substrates, both RNA and DNA. An additional heating step prior to ligation is often added to processes to reduce the undesirable secondary structures. Due to its thermostability, the TS2126 RNA ligase enzyme can be utilized at higher temperatures which can reduce these undesirable secondary structures. Additionally, the TS2126 RNA ligase has increased specific activity and efficiency and is useful not only in nucleic acid research, but also in commercial settings.

In a first aspect, the present invention relates to an isolated nucleic acid molecule which encodes a polypeptide obtainable from a thermostable bacteriophage, or an active derivative or fragment thereof, wherein the polypeptide is an RNA ligase. The polypeptide may be a thermostable RNA ligase, such as a thermostable RNA ligase obtainable from TS2126 bacteriophage, or an active derivative or fragment thereof. In one embodiment, the nucleic acid molecule encodes a polypeptide having at least 30% sequence identity with the amino acid sequence shown in SEQ ID NO:2.

The isolated nucleic acid molecule is in one embodiment comprised of the sequence shown in SEQ ID NO: 1. The isolated nucleic add may also be a nucleic acid molecule, wherein the encoded polypeptide is a derivative possessing substantial sequence identity with a polypeptide obtainable from TS2126 bacteriophage. In one embodiement, the polypeptide is an RNA ligase.

The present invention also relates to a DNA construct comprising an isolated nucleic acid molecule of the invention, operatively linked to a regulatory sequence. Such DNA constructs may for example be an expression vector. Further, the present invention relates to a host cell comprising such DNA constructs.

In a second aspect, the present invention relates to an isolated polypeptide selected from the group consisting of:
 a) a polypeptide comprising the amino add sequence of SEQ ID NO: 2;
 b) a polypeptide encoded by the nucleic acid comprising the sequence of SEQ ID NO: 1;
 c) a polypeptide having at least 30% sequence identity with the amino acid sequence of SEQ ID NO: 2; and
 d) a fragment or derivative of a), b) or c).

In one embodiment, the polypeptide is a fusion polypeptide. In another embodiment, the polypeptide has RNA ligase activity.

In a third aspect, the invention relates to a method of ligating nucleotides or nucleotide analogs or nucleic acids containing nucleotides or nucleotide analogs, comprising contacting nucleotides or nucleic adds with a thermostable RNA ligase, wherein the ligase catalyzes a reaction of ligation of the nucleotides, nucleotide analogs or nucleic acids.

The ligation may be performed at an appropriate temperature, such as at least 50° C., such as at least 60° C., such as a temperature of about 50° C. to about 75° C. The RNA ligase may in one embodiment be derived from a thermorphilic microorganism selected from the group consisting of thermophilic bacteria, archea and bacteriophage. In one embodiment, the bacteriophage is a thermostable bacteriophage. In a preferred embodiment, the thermostable bacteriophage is TS2126 bacteriophage.

The nucleotides used in the methods of the invention may be RNA or DNA, including single-stranded RNA or DNA. The nucleotide analogs may contain modified bases, modified sugars and/or modified phosphate groups.

The thermostable RNA ligase may in one embodiment be an isolated RNA ligase selected from the group consisting of:
 a) a RNA ligase obtained from a bacteriophage infecting a thermophilic bacteria;
 b) a polypeptide comprising the amino acid sequence of SEQ ID NO: 2;
 c) a polypeptide encoded by a nucleic acid comprising the sequence of SEQ ID NO: 1;
 d) a polypeptide having at. least 30% sequence identity with the amino acid sequence of SEQ ID NO: 2;
 e) a fragment or derivative of a), b), c) or d).

BRIEF DESCRIPTION OF THE DRAWINGS

The foregoing and other objects, features and advantages of the invention will be apparent from the following more particular description of preferred embodiments of the invention, as illustrated in the accompanying drawings.

FIG. 1 is the nucleic acid sequence of the open reading frame (ORF) of RNA-ligase from TS2126 (SEQ ID NO: 1).

FIG. 2 shows an amino acid sequence alignment of enterobacteria phage T4 RNA ligase and ORF-1 of TS2126 RNA ligase, the two sequences have 28% identity.

FIG. 3 is the amino acid sequence of bacteriophage T4 TS2126 RNA ligase (SEQ ID NO: 2).

FIG. 4 is the amino acid of the sequence alignment of enterobacteria phage T4 RNA ligase (SEQ ID NO: 3).

DETAILED DESCRIPTION OF THE INVENTION

Figure 5:
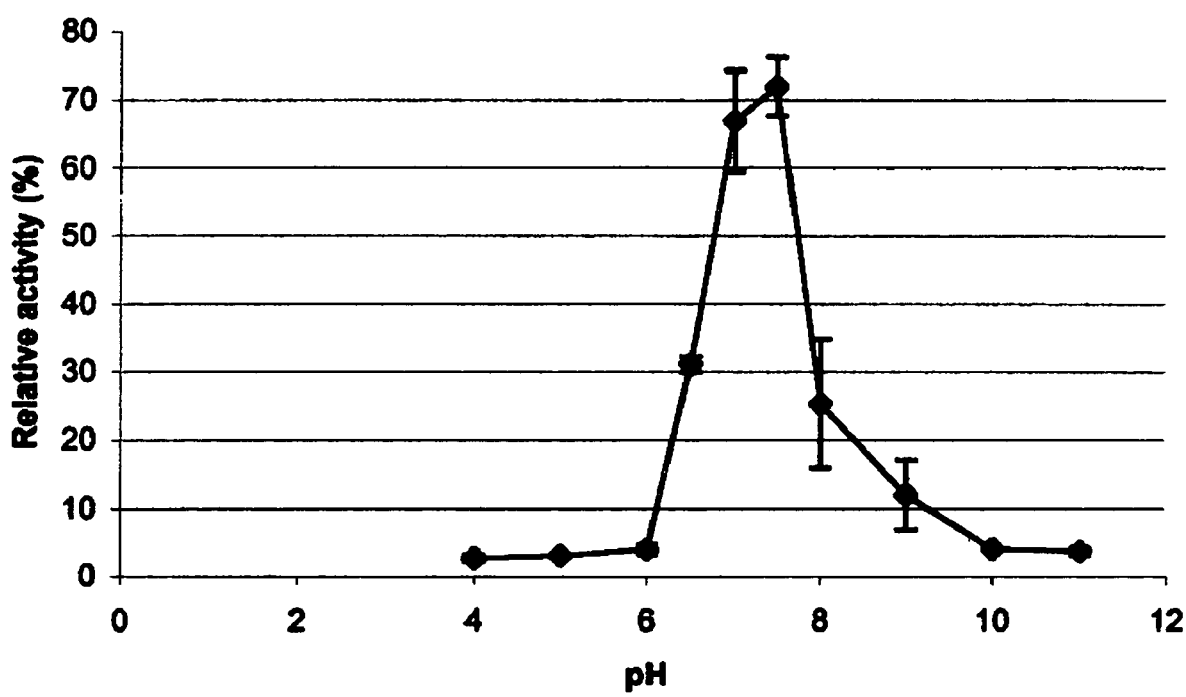
FIG. 5 shows relative activity of the TS2126 RNA ligase in MOPS buffer as a function of pH.

The present invention relates to a bacteriophage derived RNA ligase, the nucleic acid sequence of the RNA ligase, and proteins encoded by the nucleic acid sequences, as well as nucleic acid constructs comprising portions of the nucleic acid sequence of the RNA ligase, and host cells comprising such nucleic acid constructs. As described herein, Applicants have isolated and characterized a RNA ligase from bacteriophage TS2126 which infects the bacterium, *Thermus scotoductus*. The bacteriophage, TS2126, is a member of the *Myoviridae* family, with an A2 morphology (Ackerman, H. W., *Arch Virol*. 124:201-209 (1992)).

TS2126 RNA ligase can be completely stable up to about 70° C. The range of temperature for TS2126 RNA ligase activity can be greater than about 40° C., for example from about 50° C. to about 75° C. This extended range of thermostability as compared to mesophilic derived RNA ligases, such as the T4 RNA ligase, is useful in various nucleic acid techniques known to those skilled in the art and as set forth herein.

The present invention provides the characterization of a novel isolated gene product, TS2126 RNA ligase, derived from a bacteriophage from the thermophilic host *Thermus scototherrnus* and demonstrates an enzymatic activity of the isolated polypeptide similar to one of T4 RNA ligase and the previously reported ligase from *Rhodothermus marinus*, RM378 RNA ligase. Extracts containing the TS2126 RNA ligase were found to catalyze ligation of single-stranded RNA (circularization of rA20 oligonucleotide) at 60° C. The sequence identity of T4 RNA ligase and TS2126 RNA ligase is approximately 30%. Additionally, RM378 RNA ligase and TS2126 RNA ligase have a 30% sequence identity with each other.

The sequencing of the *Thermus scotothermus* bacteriophage identified an open reading frame of 1188 bases (ORF-1) as shown in FIG. 1. The amino acid sequence encoded by the open reading frame showed similarity to six public sequences having an E-value below 1 as identified in a similarity search using BLAST (Altschul, S.F., et al., *J. Mol. Biol.*, 215: 403-410 (1990)). The top scoring sequences found in the BLAST search are shown in Table 1. The most significant and extensive similarity was found to the sequence of RNA ligase from Enterobacteria phage T4. The similarities to the other sequences are much less extensive and have considerable higher E-values. The sequence identity between the ORF-1 sequence of TS2126 and the RNA ligase from T4 is 28% over 278 residues. An amino acid sequence alignment of these two enzymes is shown in FIG. 2.

TABLE 1

SEQUENCES PRODUCING SIGNIFICANT ALIGNMENTS:

| ACCESSION NUMBER | PROTEIN | ORGANISM | Score (Bits) | E-value |
|---|---|---|---|---|
| 049839.1 (NC_000866) | RNA ligase | Enterobacteria phage T4 | 75 | 3e-12 |
| 054116.1 (NC_001623) | polynucleotide kinase/ligase | *Autographa californica nucleopolyhedrovirus* | 42 | 0.023 |
| 509162.1 (NM_076761) | cuticular collagen | *C. elegans* | 39 | 0.12 |
| 602419.1 (NC_003454) | 2',3'-cyclic nucleotide 3'-phospho-diesterase | *Fusobacteriumnucleatum* subsp. *nucleatum* ATCC 25586 | 39 | 0.15 |
| AAK58479.1 | microneme protein 12 | *Toxoplasma gondii* | 39 | 0.20 |
| 558894.1 (NC_003364 | paREP2b | *Pyrobaculum aerophilum* | 37 | 0.59 |

*An E-value of 1 assigned to a hit can be interpreted as meaning that in a database of the current size one might expect to see 1 match with a similar
score simply by chance. A score indicates the relative identity between a sequence and the target sequence. The raw score is converted to a bit score
by normalizing a raw score using the formula $$S' = \frac{?S-\ln K}{\ln 2}$$

One embodiment of the invention pertains to isolated nucleic acid sequences of TS2126 RNA ligase as is shown in FIG. 1.

The nucleic acid molecules of the invention can be DNA, or can also be RNA, for example, mRNA. DNA molecules can be double-stranded or single-stranded; single stranded RNA or DNA can be either the coding, or sense, strand or the non-coding, or antisense, strand. Preferably, the nucleic acid molecule comprises at least about 100 nucleotides, more preferably at least about 150 nucleotides, and even more preferably at least about 200 nucleotides. The nucleotide sequence can be only that which encodes at least a fragment of the amino acid sequence of a polypeptide; alternatively, the nucleotide sequence can include at least a fragment of a coding sequence along with additional non-coding sequences such as non-coding 3' and 5' sequences (including regulatory sequences, for example).

Additionally, the nucleotide sequence(s) can be fused to a marker sequence, for example, a sequence which encodes a polypeptide to assist in isolation or purification of the polypeptide. Representative sequences include, but are not limited to, those which encode a glutathione-S-transferase (GST) fusion protein. In one embodiment, the nucleotide sequence contains a single ORF in its entirety (e.g., encoding a polypeptide, as described below); or contains a nucleotide sequence encoding an active derivative or active fragment of the polypeptide; or encodes a polypeptide which has substantial sequence identity to the polypeptides described herein.

The nucleic acid molecules of the invention are "isolated"; as used herein, an "isolated" nucleic add molecule or nucleotide sequence is intended to mean a nucleic acid molecule or nucleotide sequence which is not flanked by nucleotide sequences which normally (in nature) flank the gene or nucleotide sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Thus, an isolated nucleic acid molecule or nucleotide sequence can include a nucleic acid molecule or nucleotide sequence which is synthesized chemically or by recombinant means. Therefore, recombinant DNA contained in a vector are included in the definition of "isolated" as used herein. Also, isolated nucleotide sequences include recombinant DNA molecules In heterologous organisms, as well as partially or substantially purified DNA molecules In solution. In vivo and in vitro RNA transcripts of the DNA molecules of the present invention are also encompassed by "isolated" nucleotide sequences.

The present invention also pertains to nucleotide sequences which are not necessarily found in nature but which encode the polypeptides described below. Thus, DNA molecules which comprise a sequence which is different from the naturally-occurring nucleotide sequence but which, due to the degeneracy of the genetic code, encode the polypeptides of the present invention are the subject of this invention. The invention also encompasses variations of the nucleotide sequences of the invention, such as those encoding active fragments or active derivatives of the polypeptides as described below. Such variations can be naturally-occurring, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent or conserved; that is, they do not alter the characteristics or activity of the encoded polypeptide.

The invention described herein also relates to fragments of the isolated nucleic acid molecules described herein. The term "fragment" is intended to encompass a portion of a nucleotide sequence described herein which is from at least about 15, such as at least 20 or at least 25, contiguous nucleotides to at least about 50 contiguous nucleotides or longer in length; such fragments are useful as probes and also as primers. Particularly preferred primers and probes selectively hybridize to the nucleic acid molecule encoding the polypeptides described herein. For example, fragments which encode polypeptides that retain activity, as described below, are particularly useful.

The invention also pertains to nucleic acid molecules which hybridize under high stringency hybridization conditions, such as for selective hybridization, to a nucleotide sequence described herein (e.g., nucleic acid molecules which specifically hybridize to a nucleotide sequence encoding polypeptides described herein, and, optionally, have an activity of the polypeptide). Hybridization probes are oligonucleotides which bind in a base-specific manner to a complementary strand of nucleic acid. Suitable probes include polypeptide nucleic acids, as described in Nielsen, et al., *Science*, 254:1497-1500 (1991).

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity.

"High stringency conditions," "moderate stringency conditions" and "low stringency conditions" for nucleic acid hybridizations are explained on pages 2.10.1-2.10.16 and pages 6.3.1-6 in *Current Protocols in Molecular Biology* (Ausubel, F. M. et al., "Current Protocols in Molecular Biology", John Wiley & Sons, (2001)) the teachings of which are hereby incorporated by reference. The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology*, 200:546-556 (1991). Also, in, Ausubel, et al., "Current Protocols in Molecular Biology," John Wiley & Sons (2001), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of approximately 17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 minutes at room temperature; a moderate stringency wash can comprise washing in a pre-warmed solution (42° C.) solution containing 0.2×SSC/0.1% SDS for 15 min at 42° C.; and a high stringency wash can comprise washing in prewarmed (68° C.) solution containing 0.1×SSC/0.1% SDS for 15 min at 68° C. Furthermore, washes can be performed repeatedly or sequentially to obtain a desired result as known in the art.

Equivalent conditions can be determined by varying one or more of the parameters given as an example, as known in the art, while maintaining a similar degree of identity or similarity between the target nucleic add molecule and the primer or probe used. Hybridizable nucleic acid molecules are useful as probes and primers, e.g., for diagnostic applications.

Such hybridizable nucleotide sequences are useful as probes and primers for diagnostic applications. As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5 (upstream) primer that hybridizes with the 5 end of the DNA sequence to be amplified and a 3 (downstream) primer that hybridizes with the complement of the 3' end of the sequence to be amplified.

The invention also pertains to nucleotide sequences which have a substantial identity with the nucleotide sequences described herein; particularly preferred are nucleotide sequences which have at least about 10%, preferably at least about 20%, more preferably at least about 30%, more preferably at least about 40%, even more preferably at least about 50%, yet more preferably at least about 70%, still more preferably at least about 80%, and even more preferably at least about 90% identity, and still more preferably 95% identity, with nucleotide sequences described herein. Particularly preferred in this instance are nucleotide sequences encoding polypeptides having an activity of a polypeptide described herein. For example, in one embodiment, the nucleotide sequence encodes a RNA ligase, as described below.

To determine the percent identity of two nucleotide sequences, the sequences are aligned for optimal comparison purposes (e.g., gaps can be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent identity between two sequences can be accomplished using a mathematical algorithm. A preferred, non-limiting example of a mathematical algorithm utilized for the comparison of two sequences is the algorithm of Karlin, et al., *Proc. Natl. Acad. Sci. USA*, 90:5873-5877 (1993). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al., *Nucleic Acids Res*, 25:3389-3402 (1997). When utilizing BLAST and Gapped BLAST programs, the default parameters of the respective programs (e.g., NBLAST) can be used. See the programs provided by National Center for Biotechnology Information, National Library of Medicine, National Institutes of Health. In one embodiment, parameters for sequence comparison can be set at W=12. Parameters can also be varied (e.g., W=S or W=20). The value "W" determines how many continuous nucleotides must be identical for the program to identify two sequences as containing regions of identity.

The invention also provides expression vectors containing a nucleic add sequence encoding a polypeptide described herein (or an active derivative or fragment thereof), operably linked to at least one regulatory sequence. Many expression vectors are commercially available, and other suitable vectors can be readily prepared by the skilled artisan. "Operably linked" is intended to mean that the nucleotide sequence is linked to a regulatory sequence in a manner which allows expression of the nucleic acid sequence. Regulatory sequences are art-recognized and are selected to produce the polypeptide or active derivative or fragment thereof. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to bacteriophage TS2126 can be employed. It should be understood that the design of the expression vector may depend on such factors as the choice of the host cell to be transformed and/or the type of polypeptide desired to be expressed. For instance, the polypeptides of the present invention can be produced by ligating the cloned gene, or a portion thereof, into a vector suitable for expression in an appropriate host cell (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, Including, but not limited to, the gene that encodes dihydrofolate reductase and the genes that confer resistance to neomycin, tetracycline, ampicillin, chloramphenicol, kanamycin and streptomycin resistance. Thus, prokaryotic and eukaryotic host cells transformed by the described expression vectors are also provided by this invention. For instance, cells which can be transformed with the vectors of the present invention include, but are not limited to, bacterial cells such as

*Thermus scotoductus, Thermus thermophilus, E. coli* (e.g., *E. coli* K12 strains), *Streptomyces, Pseudomonas, Bacillus, Serratia marcescens* and *Salmonella typhimurium*. The host cells can be transformed by the described vectors by various methods (e.g., electroporation, transfection using calcium chloride, rubidium chloride, calcium phosphate, DEAE-dextran, or other substances; microprojectile bombardment; lipofection, infection where the vector is an infectious agent such as a retroviral genome, and other methods), depending on the type of cellular host. The nucleic add molecules of the present invention can be produced, for example, by replication in such a host cell, as described above. Alternatively, the nucleic acid molecules can also be produced by chemical synthesis.

The isolated nucleic acid molecules and vectors of the invention are useful in the manufacture of the encoded polypeptide, as probes for isolating homologous sequences (e.g., from other bacteriophage species), as well as for detecting the presence of the bacteriophage in a culture of host cells.

The nucleotide sequences of the nucleic acid molecules described herein (e.g., a nucleic acid molecule comprising SEQ ID NO: 1 as shown in FIG. 1, such as a nucleic acid molecule comprising the open reading frames can be amplified by methods known in the art. For example, this can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res*. 19, 4967 (1991); Eckert et al., *PCR Methods and Applications* 1, 17 (1991); *PCR* (eds. McPherson et al., IRL Press, Oxford); and U.S. Pat. No. 4,683,202.

Other suitable amplification methods include the ligase chain reaction (LCR) (see Wu and Wallace, *Genomics*, 4:560 (1989), Landegren, et al., *Science*, 241:1077 (1988), transcription amplification (Kwoh, et al., *Proc. Natl. Acad. Sci. USA* 86:1173 (1989)), and self-sustained sequence replication (Guatelli, et al., *Proc. Nat. Acad. Sci. USA*, 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a library or other suitable vector to identify homologous nucleotide sequences. Corresponding clones can be isolated, DNA can be obtained following in vivo excision, and the cloned insert can be sequenced in either or both orientations by art recognized methods, to identify the correct reading frame encoding a protein of the appropriate molecular weight. For example, the direct analysis of the nucleotide sequence of homologous nucleic add molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the protein(s) and the DNA encoding the protein can be isolated, sequenced and further characterized.

The invention additionally relates to isolated TS2126 RNA ligase polypeptides. The term, "polypeptide," as used herein, includes proteins, enzymes, peptides, and gene products encoded by nucleic acids described herein.

The polypeptides of the invention can be partially or substantially purified (e.g., purified to homogeneity), and/or are substantially free of other polypeptides. According to the invention, the amino acid sequence of the polypeptide can be that of the naturally-occurring polypeptide or can comprise alterations therein. Polypeptides comprising alterations are referred to herein as "derivatives" of the native polypeptide. Such alterations include conservative or non-conservative amino acid substitutions, additions and deletions of one or more amino acids; however, such alterations should preserve at least one activity of the polypeptide, i.e., the altered or mutant polypeptide should be an active derivative of the naturally-occurring polypeptide. For example, the mutation(s) can preferably preserve the three dimensional configuration of the binding site of the native polypeptide, or can preferably preserve the activity of the polypeptide (e.g., if the polypeptide is a DNA polymerase, any mutations preferably preserve the ability of the enzyme to catalyze combination of nucleotide triphosphates to form a nucleic acid strand complementary to a nucleic acid template strand). The presence or absence of activity or activities of the polypeptide can be determined by various standard functional assays including, but not limited to, assays for binding activity or enzymatic activity.

Additionally included in the invention are active fragments of the polypeptides described herein, as well as fragments of the active derivatives described above. An "active fragment," as referred to herein, is a portion of polypeptide (or a portion of an active derivative) that retains the polypeptide's activity, as described above.

Appropriate amino acid alterations can be made on the basis of several criteria, including hydrophobidty, basic or acidic character, charge, polarity, size, the presence or absence of a functional group (e.g., —SH or a glycosylation site), and aromatic character. Assignment of various amino adds to similar groups based on the properties above will be readily apparent to the skilled artisan; further appropriate amino acid changes can also be found in Bowie, et al., *Science*, 247:1306-1310 (1990). For example, conservative amino acid replacements can be those that take place within a family of amino acids that are related in their side chains. Genetically encoded amino acids are generally divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan and tyrosine are sometimes classified jointly as aromatic amino acids. For example, it is reasonable to expect that an isolated replacement of a leucine with an isoleucine or valine, an aspartate with a glutamate, a threonine with a serine or a similar conservative replacement of an amino add with a structurally related amino acid will not have a major effect on activity or functionality.

The polypeptides of the invention can also be fusion polypeptides comprising all or a portion (e.g., an active fragment) of the native bacteriophage TS2126 polypeptide amino acid sequence fused to an additional component, with optional linker sequences. Additional components, such as radioisotopes and antigenic tags, can be selected to assist in the isolation or purification of the polypeptide or to extend the half life of the polypeptide; for example, a hexahistidine tag would permit ready purification by nickel chromatography. The fusion protein can contain, e.g., a glutathione-S-transferase (GST), thioredoxin (TRX) or maltose binding protein (MBP) component to facilitate purification; kits for expression and purification of such fusion proteins are commercially available. The polypeptides of the invention can also be tagged with an epitope and subsequently purified using antibody specific to the epitope using art recognized methods. Additionally, all or a portion of the polypeptide can be fused to carrier molecules, such as immunoglobulins, for many purposes, including increasing the valency of protein binding sites. For example, the polypeptide or a portion thereof can be linked to the Fc portion of an immunoglobulin; for example, such a fusion could be to the Fc portion of an IgG molecule to create a bivalent form of the protein.

Also included in the invention are polypeptides which are at least about 30% identical (i.e., polypeptides which have substantial sequence identity) to the polypeptides described herein. However, polypeptides exhibiting lower levels of identity are also useful, particular if they exhibit higher identity over one or more particular domains of the polypeptide. For example, polypeptides sharing high degrees of identity over domains necessary for particular activities, such as binding or enzymatic activity, are included herein. Thus, polypeptides which are at least about 10%, preferably at least about 20%, more preferably at least about 30%, more preferably at least about 40%, even more preferably at least about 50%, yet more preferably at least about 70%, still more preferably at least about 80%, and even more preferably at least about 90% identity, yet more preferably at least about 95% are encompassed by the invention.

Polypeptides described herein can be isolated from naturally-occurring sources (e.g., isolated from host cells infected with bacteriophage TS2126). Alternatively, the polypeptides can be chemically synthesized or recombinantly produced. For example, PCR primers can be designed to amplify the ORFs from the start codon to stop codon, using DNA of TS2126 or related bacteriophages or respective recombinant clones as a template. The primers can contain suitable restriction sites for an efficient cloning into a suitable expression vector. The PCR product can be digested with the appropriate restriction enzyme and ligated between the corresponding restriction sites in the vector (the same restriction sites, or restriction sites producing the same cohesive ends or blunt end restriction sites).

Polypeptides of the present invention can be used as a molecular weight marker on SDS-PAGE gels or on molecular sieve gel filtration columns using art-recognized methods. They are particularly useful for molecular weight markers for analysis of proteins from thermophilic organisms, as they will behave similarly (e.g., they will not denature as proteins from mesophilic organisms would).

The polypeptides of the present invention can be isolated or purified (e.g., to homogeneity) from cell culture (e.g., from culture of host cells infected with bacteriophage T52126) by a variety of processes. These include, but are not limited to, anion or cation exchange chromatography, ethanol precipitation, affinity chromatography and high performance liquid chromatography (HPLC). The particular method used will depend upon the properties of the polypeptide; appropriate methods will be readily apparent to those skilled in the art. For example, with respect to protein or polypeptide identification, bands identified by gel analysis can be isolated and purified by HPLC, and the resulting purified protein can be sequenced. Alternatively, the purified protein can be enzymatically digested by methods known in the art to produce polypeptide fragments which can be sequenced. The sequencing can be performed, for example, by the methods of Wilm, et al. (*Nature*, 379:466-469 (1996)). The protein can be isolated by conventional means of protein biochemistry and purification to obtain a substantially pure product, i.e., 80, 95 or 99% free of cell component contaminants, as described in Jacoby, *Methods in Enzymology, Volume* 104, Academic Press, New York (1984); Scopes, *Protein Purification, Principles and Practice,* 2nd Edition, Springer-Verlag, New York (1987); and Deutscher (ed.), *Guide to Protein Purification, Methods in Enzymology*, Vol. 182 (1990).

The RNA ligase polypeptides, as described herein can be used in a similar manner as the homologous polypeptides from bacteriophage T4. For example, amplification of mRNA and synthesis of cDNA often involves the use of a complex mixture of RNA containing RNA molecules with various stable secondary structures, which inhibits the action of T4 RNA ligase. The negative influence of secondary structure has been shown using well-defined substrates, both RNA and DNA. An additional heating step prior to ligation is often added to processes to reduce the undesirable secondary structures. The limited efficiency of T4 RNA ligase using natural RNA substrates has also been demonstrated (Gumport and Uhlenbeck, in "Gene Amplification and Analysis," Vol. 11: Analysis of Nucleic Add Structure by Enzymatic Methods, Chirikjian and Papas, eds. Elsevier North Holland, Inc (1980); Bruce & Uhlenbeck, Nucleic Acids Res., 5:3665-3677 (1978); McCoy and Gumport, *Biochemistry*, 19:635-642 (1980)). The ability to carry out ligation reactions at higher temperatures using a thermostable RNA ligase, such as TS2126 RNA ligase, can limit the formation of undesirable secondary structures. The higher temperature thus improves the amplification of the RNA by increasing the proportion of RNA molecules available for ligation by the enzyme.

Potential benefits of using a thermostable RNA ligase such as TS2126 RNA ligase in place of T4 RNA ligase are discussed further. For example, the RNA ligases of bacteriophage TS2126 can be used for amplification or manipulation of DNA and RNA sequences. The enzymes of bacteriophage TS2126, particularly RNA ligase, are more thermostable than those of bacteriophage T4, because of the thermophilic nature of the host of bacteriophage TS2126 (in contrast with the mesophilic nature of *E. coli*, the host of bacteriophage T4).

Synthetic oligonucleotides have widespread use in various fields such as in molecular biology, including genetic engineering; in therapeutics, for example for antisense oligonucleotides; for diagnostics and to make catalysts as ribozymes. PCR technology, for example, routinely employs oligonucleotides as primers for amplification of genetic material and synthetic genes are made for various purposes including optimization of codon usage for efficient expression. Useful synthetic oligonucleotides include polymers containing natural ribonucleotides and deoxynucleotides as well as polymers containing modified nucleotides such as base-modified, sugar-modified and phosphate-group modified nucleotides.

After the discovery of T4 RNA ligase and early characterization of its properties, it was realized that the enzyme could be used for synthesis of oligonucleotides including oligonucleotides with a defined sequence, even complete genes of DNA or their RNA equivalents (Gumport and Uhlenbeck, "Gene Amplification and Analysis," *Vol. II: Analysis of Nucleic Acid Structure by Enzymatic Methods*, Chirikjian and Papas, eds., Elsevier North Holland, Inc. (1980); Marie, et al., *Biochemistry*, 19:635-642 (1980); Sugion, et al., *J. Biol. Chem.*, 252:1732-1738). The polypeptides of the invention are also useful in the synthesis of oligonucleotides.

In the synthesis of oligonucleotides catalyzed by T4 RNA ligase, the efficiency of the reactions can be enhanced by blocking the 3'-terminus of donor molecules and de-phosphorylating the 5'-terminus of acceptor molecules; thus driving the reaction to yield products containing a defined order of the oligonucleotide sequences. In a series of patents (U.S. Pat. Nos. 5,516,664; 5,629,177; 5,514,569 and 5,602,000), Hyman describes the synthesis of oligonucleotides by repeated cycles of combining a primer oligonucleotide and a blocked oligonucleotide using RNA ligase. The method involves the steps of: i) combining the primer and a nucleotide having a 3'-end blocked by a phosphate group in the presence of RNA ligase thereby forming an extended primer with a blocked 3'-end; ii) enzymatically removing the blocking phosphate group at the 3'-end of the extended primer using a phosphatase; and iii) repeating the previous steps using the primer-nucleotide from previous cycle (ii) as the primer in the first step (i) in the next cycle.

Using Hyman's method, the primer in each step functions as the acceptor with a free 3'-OH group and the activated adenylated nucleotide (adenylated 3',5'-bisphosphate) to be added as the donor with a 5'-phosphate group. This way, the enzymatic procedure proceeds in the 5' to 3' direction. However, Havlina describes the surprising discovery of the capability of RNA ligase to link a 3'-phosphate donor and a 5'-hydroxyl acceptor (U.S. Pat. No. 6,329,177). This allows for the synthesis of oligonucleotides in the 3' to 5' direction using RNA ligase, in opposite direction compared to the above procedure described by Hyman. In Havlina's method, RNA ligase can be used to ligate an oligonucleotide primer to a carrier molecule with a protecting group at the 5'-position or lacking a protecting group at the 3'-position. T4 RNA ligase has been used for the synthesis of circular hammer head ribozymes (Wang, L., and D. E. Ruffner. *Nucleic Adds Res.*, 26:2502-2504 (1998)), synthesis of dinucleoside polyphosphates (Atencia, E. A., et al., *Eur. J. Biochem.*, 261: 802-811 (1999)), and for the production of composite primers (Kaluz, S., et al., *BioTechniques.*, 19:182-186 (1995)).

The polypeptides of the invention can also be used for amplification of RNA, such as methods for amplification of mRNA including synthesis of the corresponding cDNA. The thermostable RNA ligase of the invention can provide advantages over the conventional T4 RNA ligase. For example, amplification of mRNA can preferably be carried out at high temperatures such as 60? C. to limit formation of secondary structures in the nucleic acid substrates that can inhibit the ligase reaction.

Several methods have been disclosed involving amplification of RNA, especially mRNA through synthesis of the corresponding cDNA. Kempe et al., in 1987 U.S. Pat. No. 4,661,450, describe a method for molecular cloning of RNA. In this method the use of RNA ligase is fundamental for the process wherein the RNA ligase is used to attach oligonucleotide linkers to the single-stranded molecule to be cloned. The attached oligonucleotides can be composed of RNA, DNA or mixture of each and facilitate the insertion of the RNA species into a cloning vector. Multiple DNA copies can then be obtained after transformation of the cloning vector into a suitable host. One disadvantage of this particular method is the requirement of having a ribonucleotide at the 3'-terminus of the linker which is attached to the 5'-terminus of the single-stranded RNA molecule to be cloned. This requirement is based on the properties of conventional RNA ligase from bacteriophage T4 which does not effectively use deoxynucleotide with the 3'-hydroxyl group of the acceptor. The use of T4 RNA ligase is thus practically limited by its substrate specificity.

More recently, methods for amplification of mRNA have mostly been based on synthesis of cDNA with the use of reverse transcriptase and amplification using PCR. Variations and improvements on the general method of synthesizing cDNA have appeared including methods to obtain cDNA of full-length RNA such as RACE (Rapid amplification of cDNA ends, Maruyama et al., *Nuclei Acids Res.*, 23:3796-7 (1995)). The methods described often involve the use of RNA ligase for ligation of nucleic acids such as for ligation of oligonucleotide to the 5'-ends of the mRNA or circularization of single-stranded cDNA. One problem associated with traditional RACE methods is the amplification of truncated cDNA (Schaefer, B. C., *Anal. Biochem.*, 227:255-273 (1995)). Ligation-mediated amplification of RNA uses RNA ligase to increase reliability of the process by preserving the termini of the RNA molecules (Volloch, et al., *Nucleic Acids Res.*, 22:2507-2511 (1994)). The presence of the cap structure on the 5'-end of full-length mRNA can be used to selectively produce cDNAs with complete length. First, a phosphatase is used to dephoshorylase mRNA molecules with a free phosphate group at the 5'-end, i.e., degraded and incomplete RNA molecules. After enzymatic removal of the cap on full-length mRNAs, linkers can be added to decapped mRNA molecules which now have a free 5'-phosphate group and can function as substrates for RNA ligase in contrast to the molecules lacking a 5'-phosphate group. A specific oligonucleotide can thus be ligated to the 5'-end of the full-length RNA molecules and cDNA can be produced using reverse transcriptase with for example a primer containing a poly(T) region complementary to the poly(A) region of eukaryotic mRNA. The cDNA can then be amplified using PCR with primers complementary to the previously ligated oligonucleotide and a gene specific primer or a primer complementary to the poly(A) region (Maruyama & Sugano 1994, Gene 138:171-174).

U.S. Pat. No. 5,597,713 describes a method of producing cDNAs with complete length by ligation of DNA or DNA-RNA chimeric oligonucleotide to the 5'-end of intact mRNAs after decapping. PCT Patent No. WO0104286 describes optimization of a method for constructing full-length cDNA libraries, by minimizing mRNA degradation and increase fullness ratio, through optimization of reaction conditions including the RNA ligase reaction. U.S. Pat. No. 6,242,189 discloses a method for selective isolation of bacterial mRNA after enzymatic modification of the mRNA such as by using RNA ligase. Merenkova et al. (U.S. Pat. No. 6,022,715) describe a method for specific coupling of the 5'-cap of the mRNA, using chemical modifications, with subsequent isolation of mRNA and preparation of complete cDNA and Zohinhöfer and Klein (PCT Patent No. WO0171027) describe a method for amplification of mRNA involving ligation of poly(C) and poly(G) flanks to cDNA.

Recently identified applications of RNA ligase are based on a target-mediated ligation of DNA by RNA ligase (U.S. Pat. No. 6,368,801). Accordingly, T4 RNA ligase can, more efficiently than T4 DNA ligase, ligate DNA ends hybridized to RNA. This property of T4 RNA ligase can be used for the detection and/or amplification of nucleic acids. Thus, known techniques based on ligation of DNA can be improved using T4 RNA ligase. These methods include ligase chain reaction (LCR), ligation-mediated PCR (LD-PCR), reverse transcription PCR combined with ligation, PCR/ligation detection reaction (PCR/LDR), oligonucleotide ligation assay (OLA), ligation-during-amplification (LDA), iterative gap ligation (IGL) and ligation of padlock probes, open circle probes and other circularizable probes.

A method for amplification of mRNA but not encompassing cDNA synthesis has been described (U.S. Pat. No. 6,338,954). This method uses RNA polymerase for amplification from an attached promoter sequence. RNA ligase is used to attach double-stranded DNA with a promoter sequence to RNA molecules.

Generally, PCR amplification procedure is based on the application of two specific primers. Therefore, in PCR screening, two conserved target sites with favourable length of interval sequence are required. Although, the method can be adapted in a high throughput manner. Most of theses single gene PCR methods have only been used on DNA samples from single species harboring limited number of genes.

One approach for single primer PCR (linear PCR) is using one gene specific primer in each PCR and then ligating an adaptor sequence to the 3' end of the single stranded copy-DNA to provide a second primer site for the second amplification step. The designed gene specific primers are affinity labeled at the 5' end (such as preferably labelled with biotin), which allows the separation of the first single stranded DNA product from the complex DNA. After several copies of the single stranded DNA have been produced by linear amplification, a second reverse priming site can be made available by ligating a single stranded oligonucleotide of known sequence to the 3' end of the single stranded DNA by a thermostable RNA ligase. The modified templates are then re-amplified by using the gene specific primer (unlabelled) and a reverse primer complementing the adapter sequence primer to make double-stranded DNA that can then be amplified by PCR for further cloning and/or sequencing.

The ligase is used for molecular cloning of RNA wherein the RNA ligase is used to attach oligonucleotide linkers to single-stranded RNA molecule to be cloned. The attached oligonucleotides can be composed of RNA, DNA or mixture of each and facilitate the insertion of the RNA species into a cloning vector. Multiple DNA copies can then be obtained after transformation of the cloning vector into a suitable host.

In preferred embodiments, amplification of mRNA can be based on synthesis of cDNA with the use of reverse transcriptase and amplification using PCR. These embodiments include methods to obtain cDNA of full-length RNA such as methods for rapid amplification of cDNA ends (RACE, Maruyama, et al., *Nucleic Acids Res.*, 23:3796-7 (1995)). These embodiments involve the use of RNA ligase for ligation of nucleic acids such as for ligation of oligonucleotide to the 5'-ends of the mRNA or circularization of single-stranded cDNA. The RNA ligase can be used for ligation-mediated amplification of RNA by preserving the termini of the RNA molecules. The presence of the cap structure on the 5'-end of full-length mRNA can be used to selectively produce cDNAs with complete length. As an example, the process essentially comprises the following steps: i) a phosphatase, such as alkaline phosphatase, is used to dephoshorylase mRNA molecules with a free phosphate group at the 5'-end, i.e. degraded and incomplete RNA molecules which lack a 5'-cap; ii) the 5'-cap on full-length mRNAs is removed such as by enzymatic removal such as by using the enzyme tobacco acid pyrophosphatase (TAP); iii) the thermostable RNA ligase is used to add linkers to the 5'-end of decapped mRNA molecules; iv) cDNA is synthesized using reverse transcriptase such as by using a primer containing a poly(T) region complementary to a poly(A) region of the mRNA; and v) the cDNA is amplified such as by using PCR such as with primers complementary to the previously ligated oligonucleotide and a gene specific primer or a primer complementary to a poly(A) region.

The linkers added to the 5'-end of RNA molecules can comprise oligonucleotides composed of RNA, DNA, DNA-RNA chimeric oligonucleotides or nucleotide analogues. For amplification of mRNA, the mRNA can be eukaryotic, archaeal or bacterial mRNA. In another embodiment, the 5'-cap can be modified using chemical modifications instead of being enzymatically removed. In another embodiment, the amplification of mRNA includes ligation of poly(C) and poly(G) flanks to the cDNA.

The polypeptides of the invention can further be used in methods for target-mediated ligation of DNA, such as is described in U.S. Pat. No. 6,368,801. The enzyme is used to ligate DNA ends hybridized to RNA, for the detection and/or amplification of nucleic acids. Known techniques based on ligation of DNA can be improved using a thermostable ligase. These methods include ligase chain reaction (LCR), ligation-mediated PCR (LD-PCR), reverse transcription PCR combined with ligation, PCR/ligation detection reaction (PCR/LDR), oligonucleotide ligation assay (OLA), ligation-during-amplification (LDA), iterative gap ligation (IGL) and ligation of padlock probes, open circle probes and other circularizable probes.

The invention is also directed to methods using the RNA ligase for amplification of mRNA without cDNA synthesis (U.S. Pat. No. 6,338,954). This method uses RNA polymerase for amplification from an attached promoter sequence. The RNA ligase is used to attach double-stranded DNA with a promoter sequence to RNA molecules.

The polypeptides of the invention can be utilized in single primer PCR (linear PCR). The process can be carried out by using one gene specific primer in each PCR and then ligate an adaptor sequence to the 3' end of the single stranded copy-DNA to provide a second primer site for the second amplification step.

T4 RNA ligase has been used in fluorescence-, isotope or biotin-labeling of the 5'-end of DNA/RNA molecules (Kinoshita et al., *Nucl. Acid Res.*, 26:2502-2504 (1997)). Thus, the polypeptides of the invention can also be used for labeling of nucleic acids. RNA ligase can be used for the labeling of oligonucleotide probes, primers or template molecules or polynucleotide probes or template molecules with nucleotide or oligonucleotide labeled with a chemical group.

Labeling of the nucleic acid (probe or primers) with the RNA ligase can be carried out prior to or following hybridization (cf. PCT WO97/27317). The chemical group can immobilize the hybrid probe/template molecule on a solid surface (see for example U.S. Pat. No. 5,595,908) or it can serve as a ligand which binds to a molecule (antibody) coupled with an enzymatically active group, thus allowing measuring of enzymatic activity and thereby achieving quantitative measure of the specific nucleotide acid in said sample.

Labeled DNA or RNA molecules can be used in various methods of quantitatively detecting nucleic acids and for detection of polynucleotide hybridization. The hybridization of DNA or RNA template molecules with the labeled nucleic acid probes can be carried out in a solution (see for example U.S. Pat. No. 6,136,531) or on a solid surface. if the hybridization takes place on a solid surface, either the nucleic add probes or the template DNA can be immobilized prior the hybridization. Further, the different probes can be immobilized and organized in an array. The hybrid template/probe molecules can be detected in solution or immobilized on a solid surface.

The polypeptides of the invention can also be used in detection assays for nucleic acids such as in diagnostics assays. This includes detection in various samples such as the detection of DNA contamination in biopharmaceuticals or detection of rare nucleic acids in clinical samples. Template nucleic acid molecules to be detected can be hybridized with binary nucleotide probes complementary to adjacent portions of the target sequence. Following hybridization the probes can be ligated with the RNA ligase in a template dependent manner. The template nucleic acid can be DNA or RNA and the primer molecules can be DNA or RNA. The ligation product can be detected with PCR amplification using appropriate primers, nucleotides and polymerases. The ligation chain reaction (LCR) can also be used for the detection of the ligation product. One of the primers or both can be labeled with radioactive, fluorescent, or electrochemiluminescent molecule, or ligand, which can bind to a molecule (antibody) coupled with an enzymatically active group, thus allowing quantitative measure of the specific nucleotide acid in said sample. Another embodiment of this method is to use a probe, which is complementary to the 5' and 3' ends of the target nucleic acid. The ends hybridize to adjacent portions of the target DNA and can be ligated with a thermostable RNA ligase in a template dependent manner thus circularizing the probe. Following ligation, one complementary primer can be added to the circular template and subsequently primer extension can be performed. Also, two primers can be added to the circular template, one reverse complementary and another forward primer, to amplify the circular template. Either the primer or the dNTPs in the PCR reaction can be labeled with radioactive, fluorescent, or electrochemiluminescent molecule, or ligand, which can bind to a molecule (antibody) coupled with an enzymatically active group, thus allowing detection and quantitative measure of the amplification product.

The polypeptides of the invention can further be used in methods of sequencing short oligonucleotides. The method can essentially comprise the following: an auxiliary oligonucleotide is ligated to the 3'-end of a target oligonucleotide with the thermostable RNA ligase. A labeled primer complementary to the auxiliary oligonucleotide is hybridized to the ligation product. The auxiliary oligonucleotide can be sequenced with the Sanger dideoxy method (*PNAS USA*, 74:5463-5467 (1977)).

The polypeptides of the invention can further be used in the analysis of single nucleotide polymorphisms and detection of mutations. The enzyme can be used in ligase-polymerase mediated genetic bit analysis of single nucleotide polymorphisms. Essentially, two oligonucleotide primers are hybridized to adjacent portions of a target molecule, separated by one nucleotide. One of the primers can be immobilized to a solid support such that the hybridization products will be immobilized. Following immobilization, polymerase extension with corresponding nucleoside triphosphate species, complementary to the nucleotide of said pre selected site, is performed to fill the space between the primers. RNA ligase is then used in the ligation of the extended primer with the downstream primer. Either one of the primers or the dNTP can be labeled for the detection of the extension-ligation product. in another embodiment of the invention, the RNA ligase can be used for detection of mutations, i.e., in direct sequence identification of mutations by cleavage and ligation associated mutation-specific sequencing. The DNA molecule, containing mutations (single base substitutions, insertions, deletions) is immobilized to a solid support. Oligos, which do not contain the alteration, are hybridized to the immobilized DNA molecule. Thus, heteroduplex is formed at the mismatch site. in the next step, the hybrids are treated with enzymes such as resolvases, mismatch repair proteins, nucleotide excision repair proteins or combinations thereof so that one or both DNA strands are cleaved within, or in the vicinity of the mismatch region. Example of a resolvase is endonuclease VII from bacteriophage T4. Examples of mismatch proteins are MutY from *E. coli* and the MutS, MutL, and MutH system in *E. coli*. Examples of nucleotide excision repair proteins are UvrA, B, C and D. The hybrids formed between the wild-type DNA and the altered DNA (with mutations) are then dissociated by denaturation, and the wild-type DNA and any cleavage product of the target DNA are removed by washing. Then the immobilized remaining target DNA is ligated with the RNA ligase to an oligonucleotide linker of predetermined sequence. This linker serves as a binding site for a sequencing primer. The sequence of the DNA immediately adjacent to the ligated oligonucleotide is then determined by sequence analysis, e.g., by using the Sanger dideoxy method (*PNAS USA*, 74:5463-5467 (1977)).

The nucleic acids of the invention, which encode, TS2126 RNA ligase can also be used in the processing of detector molecules, such as in a SELEX process and for Q-beta technology (Ellington and Szostak, *Nature*, 346:818-22 (1990)). The detector molecules can be used for the detection of any analytes with RNA affinity such as proteins, nucleotides or amino acids, vitamins, antibiotics, carbohydrates, to which they form a complex through non-nucleic acid base pairing interactions. They can be used in the diagnosis of cancer, infectious and inherited diseases. Each detector molecule consists of three functional parts, each serving a special purpose: one is ligand with high affinity to the target analyte, one is ligated to the corresponding part in the second molecule, one is a template that can be amplified by Q-beta replicase after the ligation of two RNA molecules by RNA ligase. To select specific detector molecules against a defined analyte a library of RNA molecules consisting of the three functional parts are added to a sample with pure analyte. RNA-molecules containing functional part with high affinity to the analyte, bind and form a RNA-target molecule complex. RNA-ligase is then used to ligate two RNA molecules in the complex. Consequently a template for the Q-beta replicase is formed, which enables it to replicate the detector molecule. The molecule can be amplified further by reverse transcriptase and polymerase and cloned and sequenced to analyze the composition of the detector molecule. The RNA molecules contain recognition sites for ribozymes. Following ligation, the sample is treated with ribozymes, which digests all unbound ligated RNA molecules. The specific RNA detector molecules can be produced by transcription of complement DNA sequences in plasmid downstream from promotor such as the T7 promotor. In detection assays they are added to the sample. Then RNA-ligase is added for the ligation of the two RNA molecules to form template for the Q-beta replicase. Then the molecule is amplified with Q-beta-replicase, and further with reverse transcriptase and polymerase.

While this invention has been particularly shown and described with references to preferred embodiments thereof, it will be understood by those skilled in the art that various changes in form and details may be made therein without departing from the spirit and scope of the invention as defined by the appended claims.

EXAMPLES

Example 1

Cloning, Expression and Purification of the TS2126 RNA Ligase

A clone containing the TS2126 gene was used to amplify the TS2126 gene by conventional PCR-methods. PCR products were run on a 1% agarose gel and DNA fragments of the correct size cut out. The fragments were. purified using GFX columns (Amersham Biosciences), according to manufacturer's instructions, and cut with restriction enzymes (BamHI and NdeI). The fragments were ligated into expression vector pET-23b (Novagen), cut with the same restriction enzymes, which was designed to add a histidine-tag to the C-terminus of the protein. The vector was then transformed into *E. coli* BL21-(DE3)-RIL (Strategene) and a clone selected after verification of the correct sequence by DNA sequencing. The cells were grown in a 10 L fermenter and production of the enzyme induced by IPTG in log phase. The cells were harvested and disrupted by sonication. After removal of cell debris by centrifugation was the enzyme purified using standard chromatographic techniques, first with affinity chromatography (HiTrap Chelating, Amersham Biosciences) and subsequently with gel filtration (HiPrep 26/10 Sephacryl S200 HR Amersham Biosciences) to give the final protein sample. The gene was also expressed using a Thermus host-vector system (O. H. Fridjonsson, Prokaria Ltd, personal communication) and the corresponding protein purified for comparison with the protein expressed in *E. coli*.

Example 2 pH Optimum of TS2126 RNA Ligase

The activity assay for RNA activity is based on the Phosphatase resistant assay developed by Silber et al (Proc. Natl. Acad. Sci. U.S.A. 69:3009-3013 (1972))).
Reaction conditions:

| 2 μl | 5x ligase buffer (250 mM MOPS (pH 4-11), 25 mM MgCl$_2$, 5 mM DTT, 50 mM KCl, 125 μg/ml BSA). |
|---|---|
| 0.04 μg | TS2126 RNA ligase. |
| 2 μl | $^{32}$P-5'-rA20 RNA substrate (25 μM). |
| 1 ? l | ATP (10 mM). |
| H$_2$O | to 10 μl. |

Each mixture was incubated at 60° C. for 30 minutes, and the reaction then terminated by heating at 95° C. for 5 minutes. 30 μl SAP cocktail, which includes 5U Shrimp alkaline phosphatase (SAP) in 1 ×SAP buffer (20 mM Tris-HCl (pH 8.0), 100 mM MgCl$_2$) (USB Corp. Cleveland, Ohio), was then added and incubation continued for 3 hours at 37° C. After the incubation period, 10 μl where spotted on DE81 filters (Whatman pic. Kent, UK), washed twice in 500 mM Phosphate buffers (pH 7) and dried. The filters were transferred to liquid scintillation counter vials, 5 ml OptiGold cocktail added and the filters counted for radioactivity in a liquid scintillation counter (Packard-Tricarb). The results are shown in FIG. 5.

Example 3

Temperature Optimum of TS2126 RNA Ligase

To examine the temperature optimum of the TS2126 RNA ligase, was the ligation reaction carried out at different temperatures for 30 minutes and then the activity determined by the phosphatase resistant assay (Silber et al).
Reaction conditions:

| 2 μl | 5x ligase buffer (250 mM MOPS (pH 7.5), 25 mM MgCl$_2$, 5 mM DTT, 50 mM KCl, 125 μg/ml BSA). |
|---|---|
| 0.04 μg | TS2126 RNA ligase. |
| 2 μl | $^{32}$P-5'-rA20 RNA substrate (25 μM). |
| 1 ? l | ATP (10 mM). |
| H$_2$O | to 10 μl. |

Figure 6:
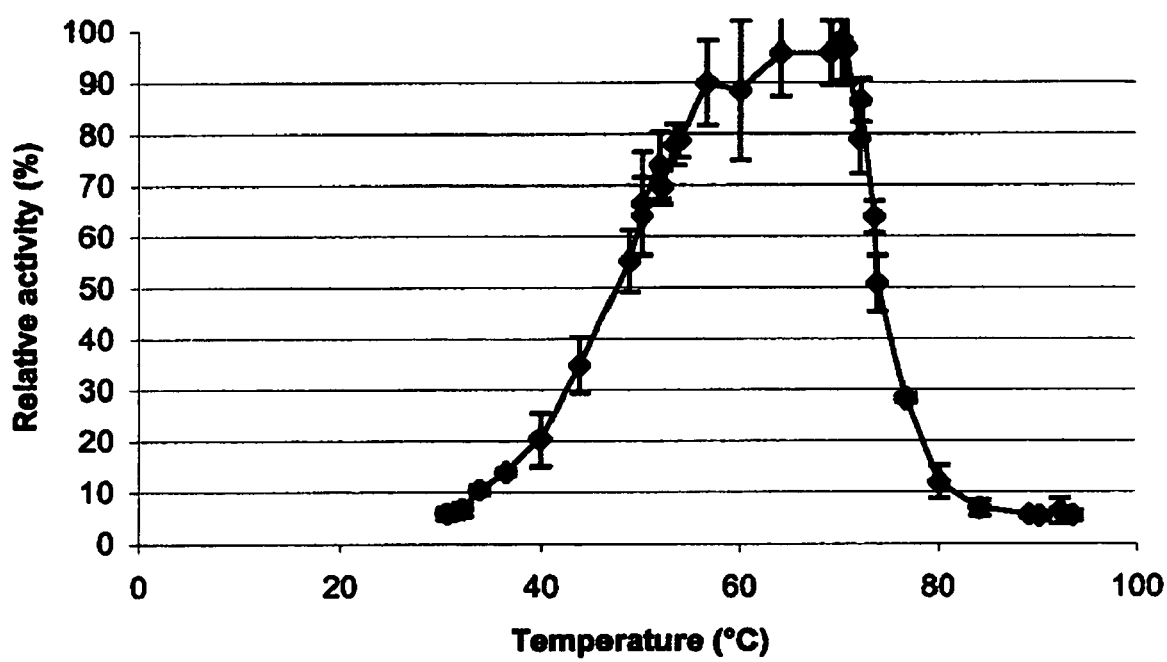
FIG. 6 shows relative activity of the TS2126 RNA ligase in MOPS buffer as a function of temperature.

The enzymatic activity of the enzyme as function of temperature is shown in FIG. 6.

Example 4

Thermostability of the TS2126 RNA Ligase

The enzyme was incubated in the reaction solution without substrate for 1 hour at 50, 60, 70, 80 and 90° C. and then substrate was added and incubated at 60° C. for 1 hour, and the samples processed as described above for the phosphatase resistant assay. The results are shown in FIG. 7.

Example 5

Figure 7:
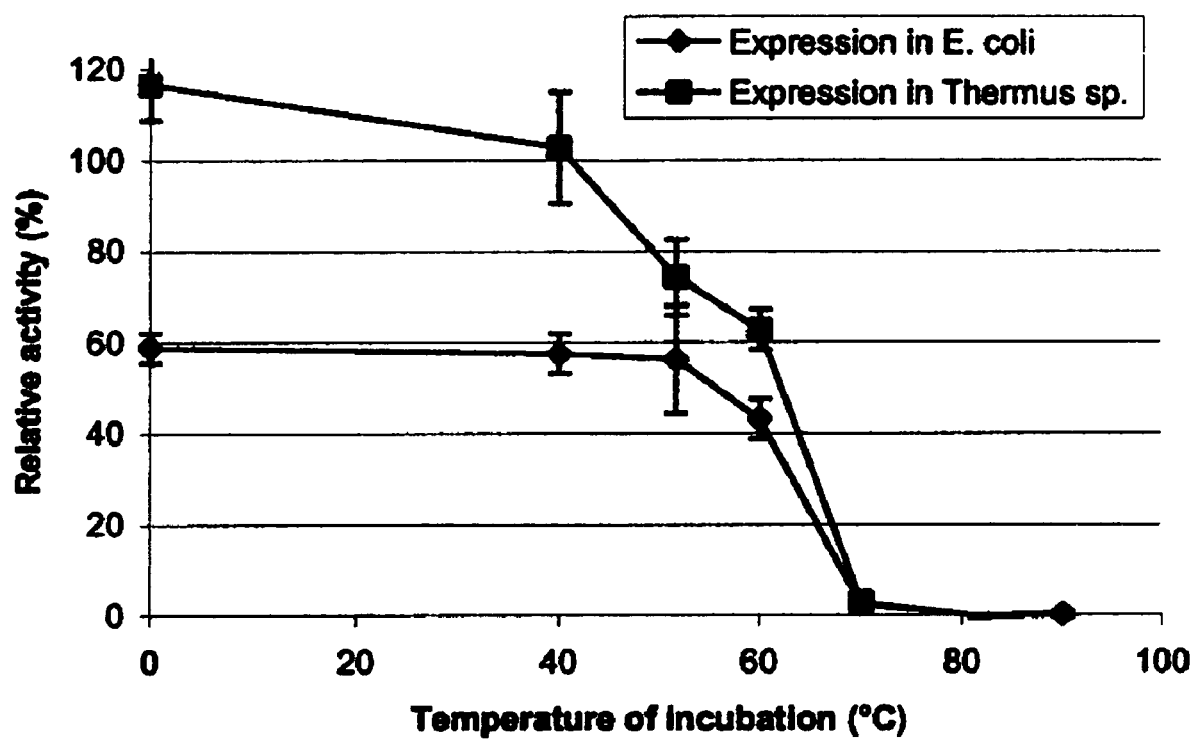
FIG. 7 shows the thermostability of the TS2126 RNA ligase at varying temperature.

In FIG. 7, the enzyme was incubated for 1 hour 50, 60, 70, 80 and 90° C. for 1 hour and activity determined. The enzyme is stable at 50° C. and looses 25% activity at 60° C. but is completely inactivated at 70° C. for 1 hour.

Effect of Cations on the TS2126 RNA Ligase Activity

The effects of varying the concentration of divalent cations, Mn2+ or Mg2+, was studied using different concentration of respective cation in the reaction buffer and the ligation reaction done as described. The results are shown in FIG. 8.

Figure 8:
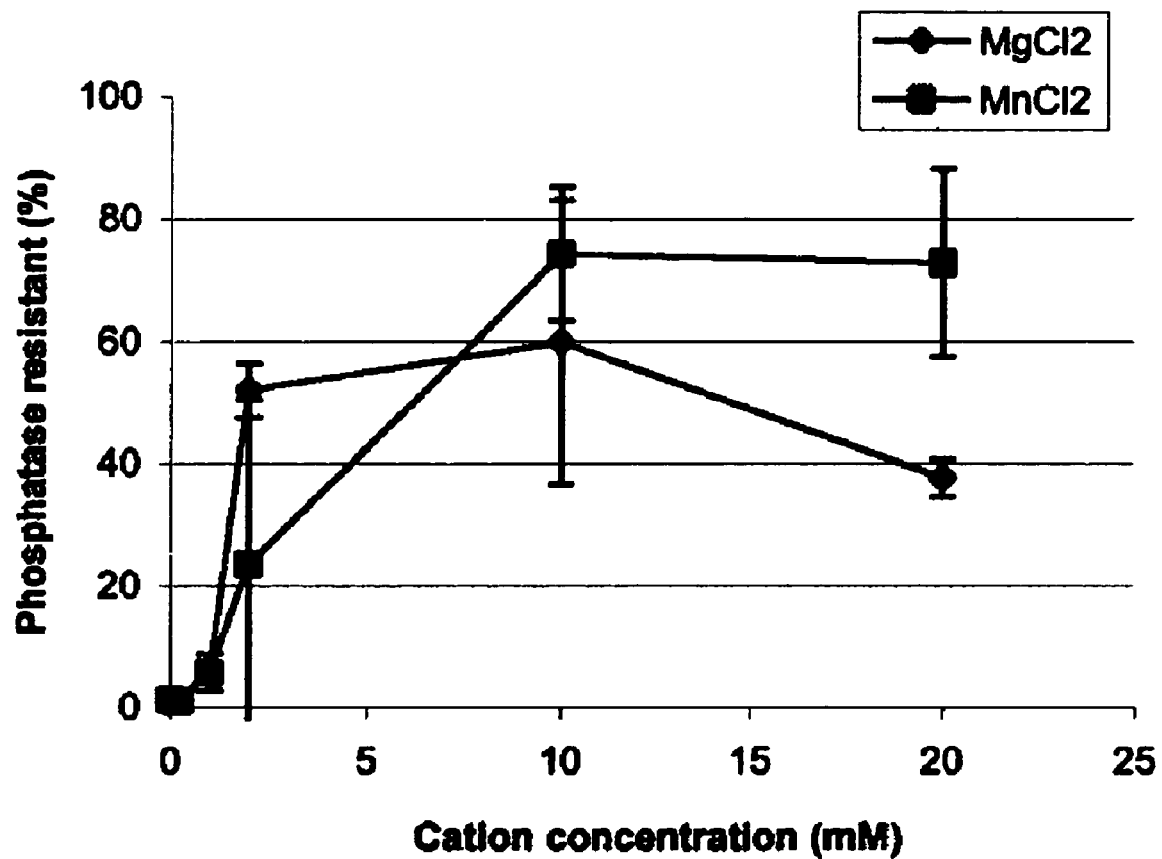
FIG. 8 shows the effects of covalent cations on the RNA ligase reaction.

FIG. 8, illustrates the results from the addition of covalent ions, necessary for the reaction. Mn$^{2+}$ gives slightly more activity than Mg$^{2+}$, but we choose to use Mg$^{2+}$ due to the destructive effect of Mn$^{2+}$ to RNA at elevated temperatures.
Reaction conditions:

| 2 μl | 5x ligase buffer (250 mM MOPS (pH 7.5), 5 mM DTT, 50 mM KCl, 125 μg/ml BSA). |
|---|---|
| 0.04 μg | TS2126 ligase. |
| 2 μl | $^{32}$P-5'-rA20 RNA substrate (25 μM). |
| 1 ? l | ATP (10 mM). |
| MgCl$_2$ or MnCl$_2$ | 0-10 mM final concentration |
| H$_2$O | to 10 μl. |

Example 6

Effects of ATP Concentration on the Activity of TS2126 RNA Ligase

Figure 9:
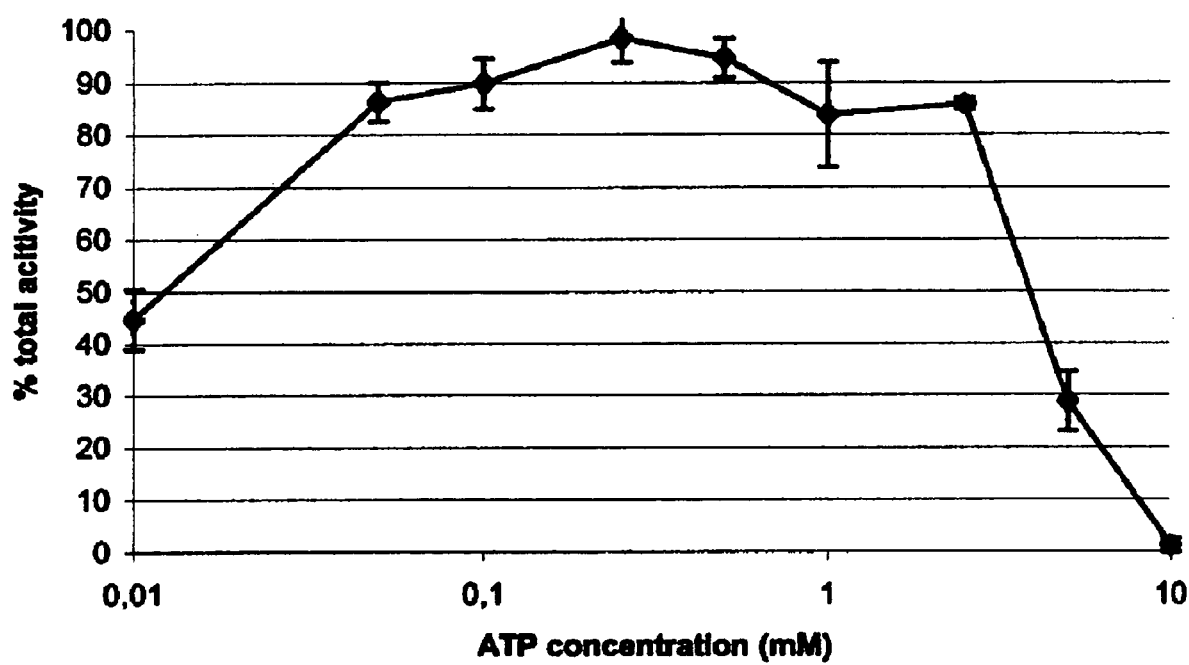
FIG. 9 shows the effect of ATP on the activity of TS2126 RNA ligase, the enzyme having over 90% activity from 0.1-2.5 mM ATP.

Effect of ATP concentration was studied by determining the activity of TS2126 RNA ligase with different amount of ATP. The results are shown in FIG. 9. We recommend 0.1-1 mM ATP concentration to be used when ligating RNA and 0.02-0.2 mM when ligating single stranded DNA.

Reaction conditions:

| | |
|---|---|
| 2 µl | 5x ligase buffer (250 mM MOPS (pH 7.5), 25 mM MgCl$_2$, 5 mM DTT, 50 mM KCl, 125 µg/ml BSA). |
| 0.04 µg | TS2126 ligase. |
| 2 µl | $^{32}$P-5'-rA20 RNA substrate (25 µM). |
| 0.01-10 mM | ATP (final concentration). |
| H$_2$O | to 10 µl. |

Example 7

Specific Activity of TS2126 RNA Ligase

The specific activities of TS2126 RNA ligase and T4 RNA ligase were compared.

Reaction conditions:

FIG. 9, illustrates that the enztme is over 90% active from 0.1-2.5 mM ATP, but is inhibited at higher concentration. Note that the x-axis is logarithmic scale.

| | |
|---|---|
| 2 µl | 5x ligase buffer (250 mM MOPS (pH 7.5), 25 mM MgCl$_2$, 5 mM DTT, 50 mM KCl, 125 µg/ml BSA). |
| 0.1 µg | TS2126 ligase. |
| 2 µl | $^{32}$P-5'-rA20 RNA substrate (25 µM). |
| 1 µl | ATP (10 mM). |
| H$_2$O | to 10 µl. |

The samples were incubated at 60° C. for 0, 2.5, 5, 15, 30, 60 and 120 minutes before determining the activity.

Figure 10:
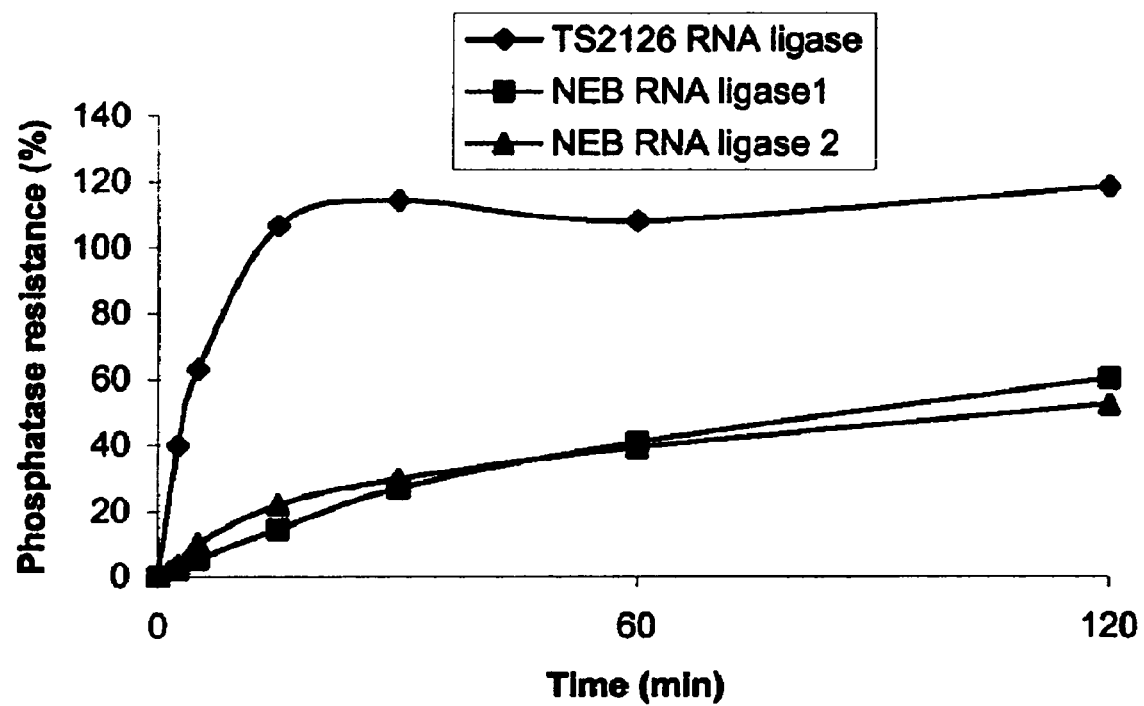
FIG. 10 shows a comparison of the activity of TS2126 and T4 RNA ligases. TS2126 RNA ligase has 10 fold higher specific activity, as compared to the T4 enzyme

The same procedure was done with T4 RNA ligase from NEB (New England Biolabs) as described by the manufacturer, using the same amount of protein (0.1 µg) and incubating at 37° C. for the same time periods. The results are shown in FIG. 10. In FIG. 10 TS2126 RNA ligase showed specific activitymore than 10 fold greater than the T4 enzyme. The specific activities were 100,000 for TS2126 and T4 (New England Biolabs) RNA ligase respectively.

Example 8

Effects of Protein Concentration on TS2126 RNA Ligase Activity

The standard RNA ligase assay was used to monitor the effect of protein concentration on the ligation of RNA substrate.

Reaction conditions:

| | |
|---|---|
| 2 µl | 5x ligase buffer (250 mM MOPS (pH 7.5), 25 mM MgCl$_2$, 5 mM DTT, 50 mM KCl, 125 µg/ml BSA). |
| 0.001-0.4 µg | TS2126 RNA ligase. |
| 2 µl | $^{32}$P-5'-rA20 RNA substrate (25 µM). |
| 1 µl | ATP (10 mM). |
| H$_2$O | to 10 µl. |

Incubated for 30 minutes at 60° C. before determining the activity. The results are shown in FIG. 11.

Figure 11:
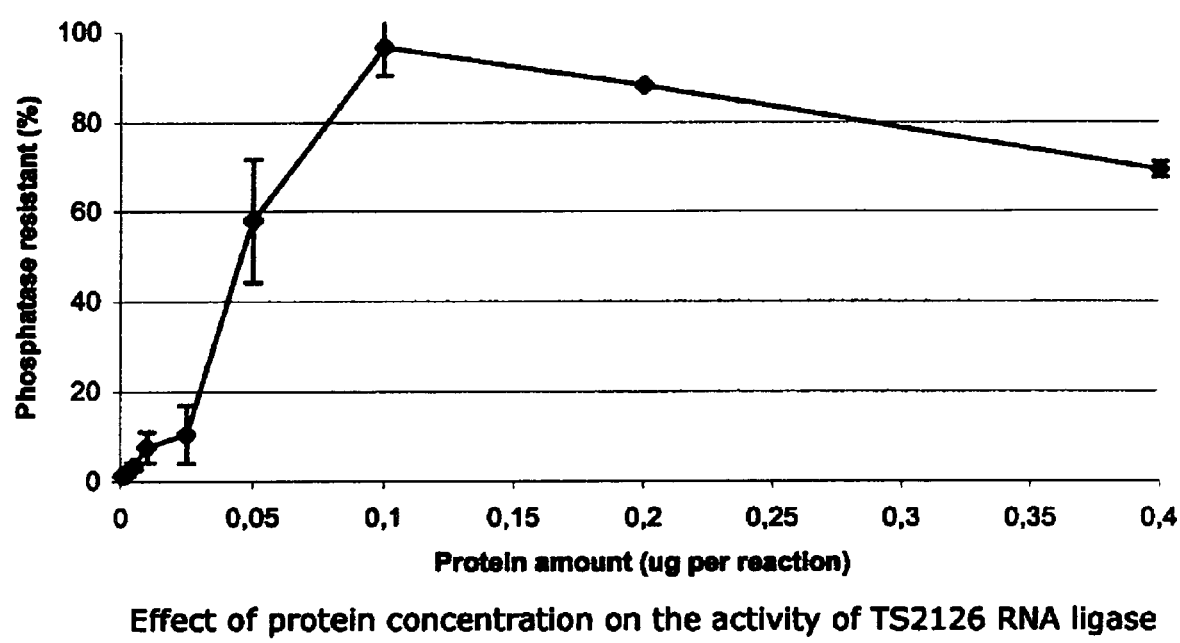
FIG. 11 shows the effect of protein concentration on the activity of TS2126 RNA ligase. Over 95% ligation was reached at 0.01 mg/ml protein concentration

In FIG. 11 the results illustrate that over 95% ligation was reached at 0.01 mg/ml protein concentration.

Example 9

TS2126 RNA Ligase in RLM-RACE Application

RLM-RACE (RNA Ligase Mediated Rapid Amplification of CDNA Ends) is one of the major application for RNA ligase in Molecular Biology. It is used to obtain 5' ends of mRNA molecules, if only a part of the sequence is known. This experiment was done using some components from the GeneRacer core kit (Invitrogen Inc.) and additional components.

Substrate for this experiment was 100 ng human testis mRNA (Ambion Inc.).

Step 1. Dephosphorylation with Calf Intestial Phosphatase (CIP) which Defosforylates all RNA except Capped mRNA Reaction conditions:

| | |
|---|---|
| Total RNA | 100 ng mRNA |
| 10x CIP buffer | 1 µl |
| RnaseOUT (40 U/µl) | 1 µl |
| CIP (10 U/µl) | 1 µl |
| DEPC treated water to | 10 µl |

The reaction was incubated for 1 hour at 50° C. and then centrifuged and put on ice. The mRNA was purified with Phenol/Cloroform extraction and ethanol precipitation before resuspending in 10 µl water Step 2: Decapping the Full Length mRNA with Tobacco Acid Pyrophosphatase (TAP)

Reaction conditions:

| | |
|---|---|
| CIP treated RNA | 7 µl |
| 10x TAP buffer | 1 µl |
| TAP(0.5 U/µl) | 1 µl |
| RNAseOUT (40 U/µl) | 1 µl |
| Total | 10 µl |

Mixed and incubated at 37° C. for 1 hour.

The RNA was purified with phenol/chloroform extraction and ethanol precipitation before resuspending in 20 µl water.

Step 3: Ligation of the Generacer RNA Oligo onto the Decapped mRNA with TS2126 RNA Ligase The ligation was done with both with T4 RNA ligase (5U per reaction) and TS2126 RNA ligase (5U per reaction):

RNA (7 µl) was mixed with pre-aliquoted, lyophilized Generacer RNA oligo (0.25 µg), mix carefully (SEQ: 5'-CGACUGGAGCACGAGGACACUGACAUG-GACUGMGGAGUAGAAA-3'). The mRNA for the T4 RNA ligase ligation was heated to 65° C. for 5 min and then spun down and put on ice, in order to minimize secundary structure. This was not done for the decapped mRNA for the TS2126 RNA ligase reaction.

Reaction conditions:

| | |
|---|---|
| Decapped RNA | 6 µl |
| 10x RNA ligase buffer | 1 µl (MOPS buffer for the TS2126 RNA ligase, and the supplied buffer with the Generacer kit for T4 RNA ligase) |

-continued

| | |
|---|---|
| ATP (10 mM) | 1 µl |
| RNAseOUT | 1 µl |
| RNA ligase (5 U/µl) | 1 µl |
| Total | 10 µl |

The reaction mixture was incubated at 37° C. for 1 hour for T4 RNA ligase and 1 hour at 60° C. for TS2126 RNA ligase. The RNA was purified with phenol/chloroform extraction and ethanol precipitation and resuspended in 10 µl water.

Step 4: cDNA Synthesis

| | | |
|---|---|---|
| Ligated RNA | 18.4 µl | |
| dT20 oligo | 1.6 µl | (1 µg) |
| Total | 20 µl | |

Incubated at 70° C. for 10 min and cooled on ice.
5×First strand synthesis buffer 6 µl

| | |
|---|---|
| PowerScript RT (Clontech) | 1.5 µl |
| dNTP mix (10 µl each) | 3 µl |
| DTT (100 mM) | 3 µl |
| RNAaseOUT (40 U/µl) | 1.5 µl |
| RNA and dT$_{20}$ mixture | 15 µl |

After incubation at 42° C. for 70 min the reaction was terminated by heating at 70° C. for 15 min and then centrifuged and put on ice. We then used 0.1-1.0 µl for 30 µl PCR reaction using GeneRacer 5' Primer (SEQ: 5'-CGACTGGAGCACGAGGACACTGA-3') or GeneRacer 5' nested primer (SEQ: 5'-GGACACTGACATGGACTGAAGGAGTA-3') and GeneRacer 5' control primer B1 (Beta actin gene specific primer) (SEQ: 5'- GACCTGGCCGTCAGGCAGCTCG-3').

The PCR protocol (Using AmpliTaq Gold® (Applied Biosystems)) was as follows, see manufacturer instructions for details:

| | |
|---|---|
| cDNA | 1 µl |
| 10x Gold buffer | 3 µl |
| MgCl$_2$ solution | 3 µl |
| AmpliTaq (5 U/? l) | 0.3 µl |
| dNTPs (2 mM) | 3 µl |
| Water | 19.7 µl |

PCR program:

| Temperature | Time | Cycles |
|---|---|---|
| 94° C. | 12 min | 1 |
| 94° C. | 30 sec | 4 |
| 72 | 2 min | |
| 94° C. | 30 sec | 4 |
| 70° C. | 2 min | |
| 94° C. | 30 sec | 30 |
| Gradient 55-70° C. | 30 sec | |
| 72° C. | 2 min | |
| 4° C. | forever | |

5 µl of the PCR product were run on a 0.8% agarose gel after the PCR.

Figure 12:
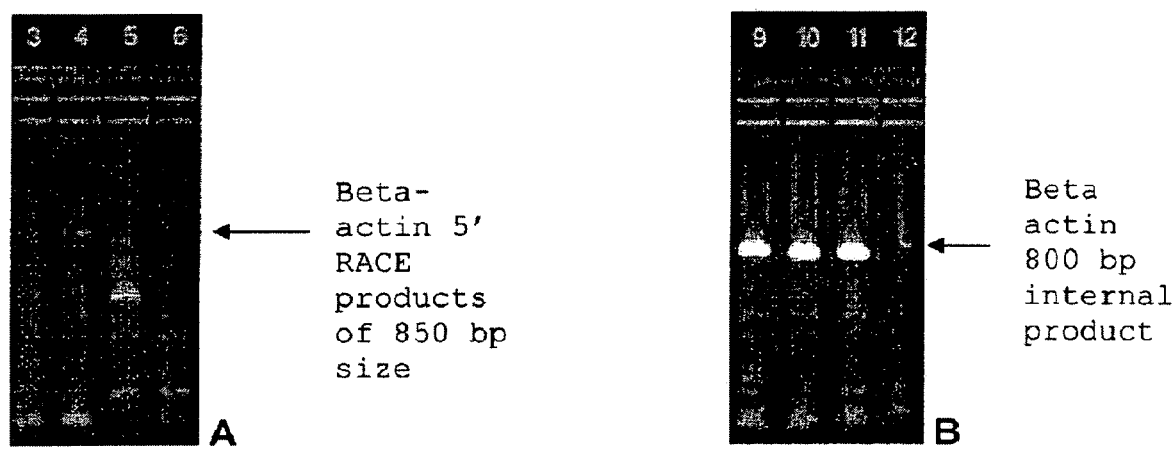
FIG. 12 shows results of RNA Ligase Mediated Rapid Amplification of cDNA Ends, showing that TS2126 RNA ligase can be used for RLM-RACE protocols at elevated temperatures and will give similar results as the standard T4 RNA ligase protocol.

Results:

As seen by the results in FIG. 12, we obtained a PCR product of similar size as expected. We therefore conclude that we can use the TS2126 RNA ligase in a RLM-RACE procedure.

As seen by results in FIG. 12, we obtained a PCR product of similar size as expected. We therefore conclude that we can use the TS2126RNA ligase in a RLM-RACE procedure. The results show that TS2126 RNA ligase can be used at elevated temperatures and will give similiar results as the standard T4 RNA ligase protocol.

Example 10

The Use of TS2126 RNA Ligase in inverse RACE Protocol

DNA circularisation of large templates for inverse RACE on the cDNA level was done by making beta actin cDNA from 500 ng testis mRNA (Ambion Inc.) Phosphorylated internal primer 5'P-B1 (5'P-GACCTGGCCGTCAGGCAGCTCG) was used in the cDNA synthesis using AMV first strand synthesis kit (Invitrogen Inc) as recommended by the manufacturer and the RNA digested with RNAseH (Ambion Inc.) as recommended by the manufacturer. The ca. 800 base long beta actin specific cDNA was then purified on PCR purification column (Qiagen Inc.), as recommended by the manufacturer, and resuspended in 30 µl water. 10 µl of the beta actin cDNA were used for each ligation.

The samples were then ligated using both 50U T4 RNA ligase and TS2126 RNA ligase in standard buffers (with PEG6000 and 1 mM hexamine cobalt chloride for T4 RNA ligase) and 20 µM ATP in a 20 µl volume at 22° C. and 60° C. respectively, for 12 hours.

The ligated samples were amplified using internal inverse primers (InvA: CTGGACTTCGAGCAAGAGATG and invB: GCCGTTGTCGACGACGAGC) over the ligation border. The reaction mixture was made as follows:

| | |
|---|---|
| Ligated cDNA | 3 µl |
| 10x Gold buffer | 3 µl |
| MgCl$_2$ solution | 3 µl |
| AmpliTaq (5 U/µl) | 0.3 µl |
| dNTPs (2 mM) | 3 µl |
| Water | 17.7 µl |

PCR program:

| Temperature | Time | Cycles |
|---|---|---|
| 94° C. | 12 min | 1 |
| 94° C. | 30 sec | 35 |
| 55 | 30 min | |
| 72° C. | 1 min | |
| 4° C. | forever | |

Figure 13:
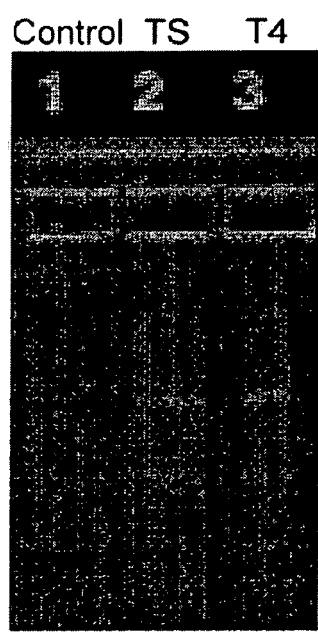
FIG. 13 presents results from an inverse beta actin PCR showing that TS2126 RNA ligase can be used for CDNA ligation.

8 µl of the PCR product were run on a 2% agarose gel. The results are shown in FIG. 13.

Example 11

DNA Intra-molecular Ligations

RNA ligases also show ligation activity on ssDNA. To measure the activity on ssDNA was 5'P-d($N_{22}$) oligonucleotide ligated (circularised) under the following conditions.
Reaction conditions:

| | |
|---|---|
| 4 µl | 5x ligase buffer (250 mM MOPS (pH 7.5), 25 mM $MgCl_2$, 5 mM DTT, 50 mM KCl, 125 µg/ml BSA). |
| 2 µg | TS2126 RNA ligase (0.1 mg/ml final concentration). |
| 2 µl | ssDNA substrate (1.5 or 50 µM) |
| 1 µl | ATP (1 mM). |
| $H_2O$ | to 20 µl. |

The reaction mixture was incubated for 2 h at 60° C. 10 µl of each sample was digested with 10 U Exonuclease 1, mixed with Oligreen reagent (Molecular Probes), and measured with Oligreen Ex/Em 490-520 nm. The remaining of the sample was measured as total and unligated samples (Exo I digested) were used for background subtraction. The samples with and without ligation were run on 4% agarose gel. The results are shown in FIG. 14.

Figure 14:
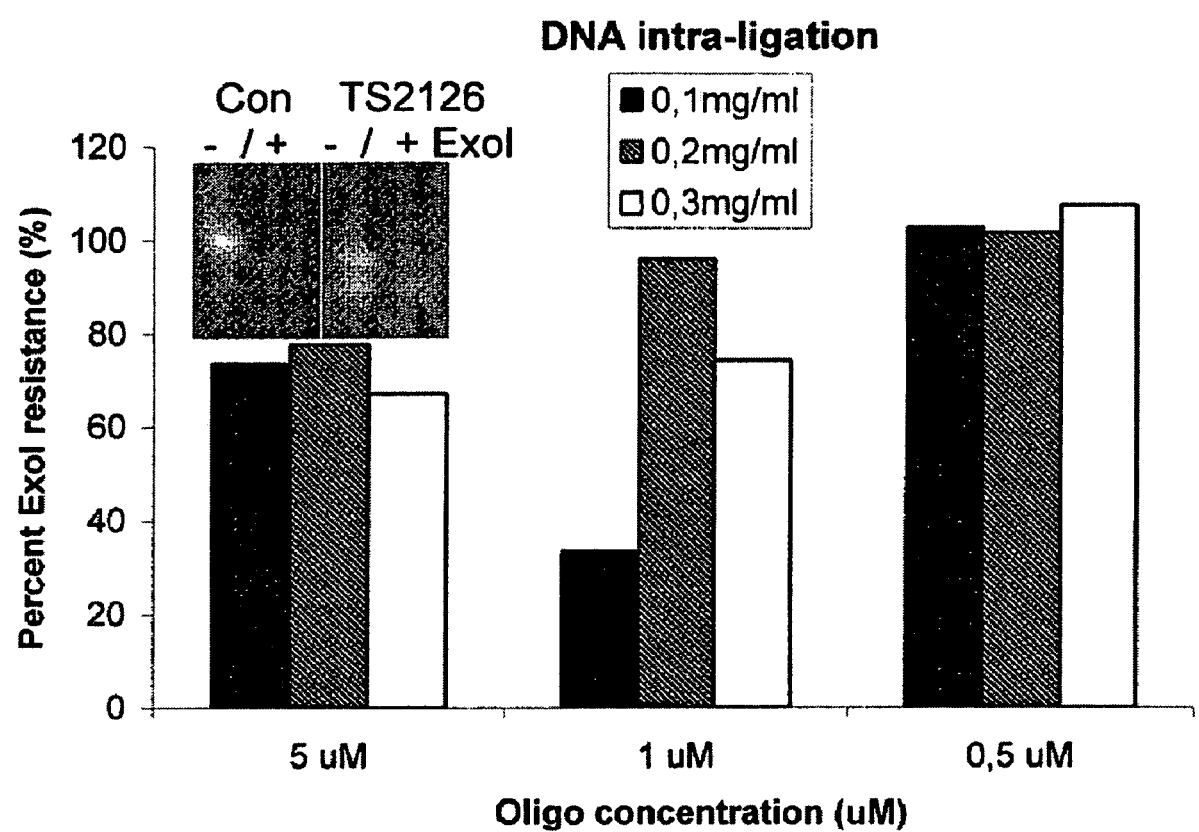
FIG. 14 shows the results of an intramolecular ligation reaction using a 22 nt oligomer. The effect of varying the protein concentration is minimal but as expected the ligation is dependent on substrate concentration.

In FIG. 14, the ligations of this 22nt oligomer show that the effect of varying the protein concentration is minimal but as expected the litigation is dependent on substrate concentration. Agarose gel in the left corner show visually the circularization and ExoI resistance.

The DNA circularisation experiments routinely give over 50% ligations after 2 hours at 60° C. using 20-100 µM ATP and 0.1 mg/ml TS2126 RNA ligase.

The addition of Hexamine cobalt chloride or PEG6000 does not significantly enhance the activity.

For comparison, T4 RNA ligase was also used for ligation of the same substrate in 0.28mg/ml conc. (1U/µl) in 0.02 mM ATP, with 1 mM hexamine cobalt chloride and 10, 20 and 30% PEG6000 at 17 and 22° C. The results are shown in FIG. 15.

Figure 15:
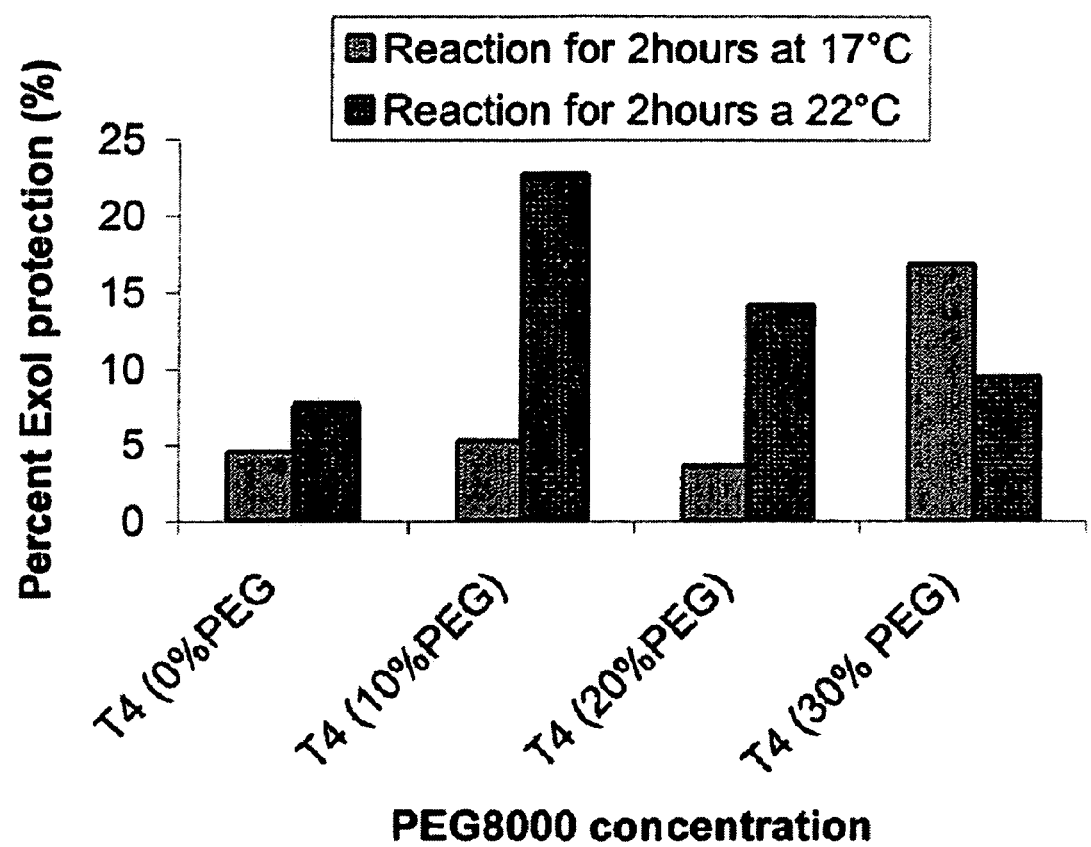
FIG. 15 shows results of an intramolecular ligation using T4 RNA ligase at both 17° C. and 22° C. using a 22 nt oligomer template. The activity of the T4 RNA ligase is much less than that of the TS2126 RNA ligase.

FIG. 15 shows the intra molecular ligation of T4 RNA ligase at both 17 and 22° C. for 2 hours using 1 uM $22^{nd}$ oligomer template. The acvtivity is much less than for TS2126 RNA ligase.

All publications, patents, and patent applications cited in this document are incorporated by reference herein in their entirety, as though individually incorporated by reference.

The invention claimed is:

1. An isolated polypeptide which is a RNA ligase selected from the group consisting of:
   a) a polypeptide comprising the amino acid sequence of SEQ ID NO: 2;
   b) a polypeptide encoded by a nucleic acid comprising the sequence of SEQ ID NO: 1; and
   c) active fragments thereof.

2. The polypeptide of claim 1, which is a fusion polypeptide.

3. An isolated thermostable RNA ligase having at least 95% sequence identity to the amino acid sequence of SEQ ID NO: 2.

4. The RNA ligase of claim 3, wherein the ligase catalyzes ligation of single-stranded DNA, wherein ligation efficiency is measured using a single-stranded 22-mer DNA 5'P-d($N_{22}$) as a substrate under the following conditions:

0.1 mg/mL ligase is reacted with 5 μM of said substrate in a solution with 1 mM ATP, 50 mM MOPS (pH 7.5), 5 mM $MgCl_2$, 1 mM DTT, 10 mM KCl, and 25 μg/mL BSA, and the ligase produces over 50% ligation of the single-stranded DNA after 2 hours at 60° C.

* * * * *

SEQUENCE LISTING

```
<160> NUMBER OF SEQ ID NOS: 3

<210> SEQ ID NO 1
<211> LENGTH: 1188
<212> TYPE: DNA
<213> ORGANISM: Bacteriophage TS2126

<400> SEQUENCE: 1
atgagctctt tggccccgtg gaggactacc tcctggagcc cgcttgggag cccgcctagc      60
ctcgaggacg ccctccgcct cgcccggacc accagggcct tcgcggtgcg gcgggacggg     120 gagggcggg ccctcgtgac ctacctctac ggcacccgg agctcttcag cctcccgggg     180
gcaagggagc tccggggcat cgtctaccgg gaggaggacg gcaccgtgct cagccgcccc     240
ttccacaagt tcttcaactt cggggagccc ctggccccgg gggaggaggc cttcaaggcc     300
ttccgggaca gcatggtccc cctcttcgtg gccgagaagg tggacggcta tctggcccag     360
gcctacctgg acggggcga gctccgcttc gcctcccggc actccctgaa cccgcccctg     420 gtagggcgc tcctgcgcaa ggccgtggac gaggaggcga tggctcgcct ggggaagctc     480
ctcgccgccg aaggggaag gtggacgcg cttttggagg tggtggaccc cgaggccccg     540
gtgatggtgc cctaccagga gcccgggtc tacctcctgg ccctgaggag catcggggag     600
gggcactacc tcctccccgg ggtccacttc ccctgcccg aggcgctccg ctacgtgcgg     660
tgggagccca ggatggattt tgaccccac cgcttccggg gggagatcag ggacctccag     720
ggggtggagg ggtacgtggt cacggacggg gcagagttcg tcaagttcaa gacagggtgg     780
gccttccgcc tcgcccgctt cctcatggac ccggaggggg tgttcctcga ggcctacgcc     840
gaggaccgcc tagacgacct cgtgggcgcc ctcgcgggc gggaggacct cctgcgggcg     900
gtggccaggg cccaggacta cctcgccggg ctctacgggg aagcggtggg cgcgggggac     960
gccctgaggc ggatgggcct cccccggaag gaggcctggg cccgggtgca ggaggaggcc    1020
```

```
gggcgctggg gcggcttcgc ccccgcctac gcccgggcgg ccatggcggc ctacgagggg   1080
ggagaggcgc gcgaggcctt cctggtggag ctcaggaaga ggagcgcgcg gaaggccctc   1140
gaggcgctcc acctcttccc ccgggtgggc ggggagctta gggggtga                1188
```

<210> SEQ ID NO 2
<211> LENGTH: 395
<212> TYPE: PRT
<213> ORGANISM: Bacteriophage TS2126

<400> SEQUENCE: 2

```
Met Ser Ser Leu Ala Pro Trp Arg Thr Thr Ser Trp Ser Pro Leu Gly
1               5                   10                  15

Ser Pro Pro Ser Leu Glu Asp Ala Leu Arg Leu Ala Arg Thr Thr Arg
            20                  25                  30

Ala Phe Ala Val Arg Arg Asp Gly Glu Gly Arg Ala Leu Val Thr Tyr
        35                  40                  45

Leu Tyr Gly Thr Pro Glu Leu Phe Ser Leu Pro Gly Ala Arg Glu Leu
    50                  55                  60

Arg Gly Ile Val Tyr Arg Glu Glu Asp Gly Thr Val Leu Ser Arg Pro
65                  70                  75                  80

Phe His Lys Phe Phe Asn Phe Gly Glu Pro Leu Ala Pro Gly Glu Glu
                85                  90                  95

Ala Phe Lys Ala Phe Arg Asp Ser Met Val Pro Leu Phe Val Ala Glu
            100                 105                 110

Lys Val Asp Gly Tyr Leu Ala Gln Ala Tyr Leu Asp Gly Gly Glu Leu
        115                 120                 125

Arg Phe Ala Ser Arg His Ser Leu Asn Pro Pro Leu Val Gly Ala Leu
    130                 135                 140

Leu Arg Lys Ala Val Asp Glu Glu Ala Met Ala Arg Leu Gly Lys Leu
145                 150                 155                 160

Leu Ala Ala Glu Gly Gly Arg Trp Thr Ala Leu Leu Glu Val Val Asp
                165                 170                 175

Pro Glu Ala Pro Val Met Val Pro Tyr Gln Glu Pro Gly Val Tyr Leu
            180                 185                 190

Leu Ala Leu Arg Ser Ile Gly Glu Gly His Tyr Leu Leu Pro Gly Val
        195                 200                 205

His Phe Pro Leu Pro Glu Ala Leu Arg Tyr Val Arg Trp Glu Pro Arg
    210                 215                 220

Met Asp Phe Asp Pro His Arg Phe Arg Gly Glu Ile Arg Asp Leu Gln
225                 230                 235                 240

Gly Val Glu Gly Tyr Val Val Thr Asp Gly Ala Glu Phe Val Lys Phe
                245                 250                 255

Lys Thr Gly Trp Ala Phe Arg Leu Ala Arg Phe Leu Met Asp Pro Glu
            260                 265                 270

Gly Val Phe Leu Glu Ala Tyr Ala Glu Asp Arg Leu Asp Asp Leu Val
        275                 280                 285

Gly Ala Leu Ala Gly Arg Glu Asp Leu Leu Arg Ala Val Ala Arg Ala
    290                 295                 300

Gln Asp Tyr Leu Ala Gly Leu Tyr Gly Glu Ala Val Gly Ala Gly Asp
305                 310                 315                 320

Ala Leu Arg Arg Met Gly Leu Pro Arg Lys Glu Ala Trp Ala Arg Val
                325                 330                 335

Gln Glu Glu Ala Gly Arg Trp Gly Gly Phe Ala Pro Ala Tyr Ala Arg
            340                 345                 350
```

Ala Ala Met Ala Ala Tyr Glu Gly Gly Glu Ala Arg Glu Ala Phe Leu
            355                 360                 365

Val Glu Leu Arg Lys Arg Ser Ala Arg Lys Ala Leu Glu Ala Leu His
        370                 375                 380

Leu Phe Pro Arg Val Gly Gly Glu Leu Arg Gly
385                 390                 395

<210> SEQ ID NO 3
<211> LENGTH: 374
<212> TYPE: PRT
<213> ORGANISM: Bacteriophage T4

<400> SEQUENCE: 3

Met Gln Glu Leu Phe Asn Asn Leu Met Glu Leu Cys Lys Asp Ser Gln
1               5                   10                  15

Arg Lys Phe Phe Tyr Ser Asp Asp Val Ser Ala Ser Gly Arg Thr Tyr
            20                  25                  30

Arg Ile Phe Ser Tyr Asn Tyr Ala Ser Tyr Ser Asp Trp Leu Leu Pro
        35                  40                  45

Asp Ala Leu Glu Cys Arg Gly Ile Met Phe Glu Met Asp Gly Glu Lys
50                  55                  60

Pro Val Arg Ile Ala Ser Arg Pro Met Glu Lys Phe Phe Asn Leu Asn
65                  70                  75                  80

Glu Asn Pro Phe Thr Met Asn Ile Asp Leu Asn Asp Val Asp Tyr Ile
                85                  90                  95

Leu Thr Lys Glu Asp Gly Ser Leu Val Ser Thr Tyr Leu Asp Gly Asp
            100                 105                 110

Glu Ile Leu Phe Lys Ser Lys Gly Ser Ile Lys Ser Glu Gln Ala Leu
        115                 120                 125

Met Ala Asn Gly Ile Leu Met Asn Ile Asn His His Arg Leu Arg Asp
130                 135                 140

Arg Leu Lys Glu Leu Ala Glu Asp Gly Phe Thr Ala Asn Phe Glu Phe
145                 150                 155                 160

Val Ala Pro Thr Asn Arg Ile Val Leu Ala Tyr Gln Glu Met Lys Ile
                165                 170                 175

Ile Leu Leu Asn Val Arg Glu Asn Glu Thr Gly Glu Tyr Ile Ser Tyr
            180                 185                 190

Asp Asp Ile Tyr Lys Asp Ala Thr Leu Arg Pro Tyr Leu Val Glu Arg
        195                 200                 205

Tyr Glu Ile Asp Ser Pro Lys Trp Ile Glu Glu Ala Lys Asn Ala Glu
210                 215                 220

Asn Ile Glu Gly Tyr Val Ala Val Met Lys Asp Gly Ser His Phe Lys
225                 230                 235                 240

Ile Lys Ser Asp Trp Tyr Val Ser Leu His Ser Thr Lys Ser Ser Leu
                245                 250                 255

Asp Asn Pro Glu Lys Leu Phe Lys Thr Ile Ile Asp Gly Ala Ser Asp
            260                 265                 270

Asp Leu Lys Ala Met Tyr Ala Asp Glu Tyr Ser Tyr Arg Lys Ile
        275                 280                 285

Glu Ala Phe Glu Thr Thr Tyr Leu Lys Tyr Leu Asp Arg Ala Leu Phe
290                 295                 300

Leu Val Leu Asp Cys His Asn Lys His Cys Gly Lys Asp Arg Lys Thr
305                 310                 315                 320

Tyr Ala Met Glu Ala Gln Gly Val Ala Lys Gly Ala Gly Met Asp His
                325                 330                 335

-continued

```
Leu Phe Gly Ile Ile Met Ser Leu Tyr Gln Gly Tyr Asp Ser Gln Glu
            340                 345                 350

Lys Val Met Cys Glu Ile Glu Gln Asn Phe Leu Lys Asn Tyr Lys Lys
            355                 360                 365

Phe Ile Pro Glu Gly Tyr
    370
```